(12) United States Patent
Morales

(10) Patent No.: US 11,931,101 B2
(45) Date of Patent: *Mar. 19, 2024

(54) APPARATUS, SYSTEMS AND METHODS FOR TRANSVASCULAR ACCESS TO THE BRAIN

(71) Applicant: VONOVA INC., Oceanside, CA (US)

(72) Inventor: Jose Miguel Morales, Los Angeles, CA (US)

(73) Assignee: VONOVA INC., Oceanside, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/114,906

(22) Filed: Feb. 27, 2023

(65) Prior Publication Data

US 2023/0200898 A1 Jun. 29, 2023

Related U.S. Application Data

(63) Continuation of application No. 17/956,382, filed on Sep. 29, 2022, which is a continuation of application
(Continued)

(51) Int. Cl.
*A61B 18/14* (2006.01)
*A61B 5/00* (2006.01)
(Continued)

(52) U.S. Cl.
CPC .......... *A61B 18/1492* (2013.01); *A61B 5/293* (2021.01); *A61B 5/6853* (2013.01);
(Continued)

(58) Field of Classification Search
CPC .. A61B 2018/0016; A61B 2018/00166; A61B 5/293; A61B 5/26853;
(Continued)

(56) References Cited

U.S. PATENT DOCUMENTS 4,552,554 A * 11/1985 Gould ................... A61M 25/01
604/164.13
4,669,469 A 6/1987 Gifford, III et al.
(Continued)

FOREIGN PATENT DOCUMENTS

WO      WO 98/16161 A1    4/1998
WO    WO2016/131020 A1    8/2016

OTHER PUBLICATIONS

Search Report and Written Opinion issued in International Application No. PCT/US2020/041246, dated Oct. 28, 2020 (6 pages).
(Continued)

*Primary Examiner* — Eun Hwa Kim
(74) *Attorney, Agent, or Firm* — BLAIR WALKER IP SERVICES, LLC

(57) ABSTRACT

The present disclosure discusses a devices, systems and methods for transvascular, transvenous and/or transdural access, to the brain parenchyma, subarachnoid or subdural spaces. In some embodiments, the disclosed systems and methods may be used for local drug delivery, tissue biopsy, nanofluidic or microelectronic device/component delivery/insertion/implantation, in situ imaging, ablation of abnormal brain tissue and the like. Embodiments of the present disclosure include an access catheter system for extravascular procedures in the brain having an elongate, flexible tubular body, with at least one lumen extending axially there through between a proximal end, and a distal end. The access catheter system may include a side exit port and a distal end port. Further, the access catheter system may include a selective deflector positioned within the lumen configured to deflect a procedure catheter and permit a guide catheter.

29 Claims, 18 Drawing Sheets

Related U.S. Application Data

No. 17/624,225, filed as application No. PCT/US2020/041246 on Jul. 8, 2020, now Pat. No. 11,497,552.

(60) Provisional application No. 62/871,976, filed on Jul. 9, 2019.

(51) Int. Cl.
| | |
|---|---|
| *A61B 5/293* | (2021.01) |
| *A61B 90/00* | (2016.01) |
| *A61N 1/05* | (2006.01) |
| *A61N 1/36* | (2006.01) |
| *A61B 18/00* | (2006.01) |
| *A61M 25/00* | (2006.01) |
| *A61M 25/10* | (2013.01) |

(52) U.S. Cl.
CPC .......... *A61B 5/6859* (2013.01); *A61B 5/6868* (2013.01); *A61B 90/37* (2016.02); *A61N 1/0534* (2013.01); *A61N 1/36067* (2013.01); *A61N 1/36082* (2013.01); *A61B 2018/0016* (2013.01); *A61B 2018/00166* (2013.01); *A61B 2018/00285* (2013.01); *A61B 2018/00446* (2013.01); *A61B 2018/00577* (2013.01); *A61B 2018/0063* (2013.01); *A61B 2018/00791* (2013.01); *A61B 2018/00839* (2013.01); *A61B 2090/064* (2016.02); *A61B 2090/363* (2016.02); *A61B 2090/378* (2016.02); *A61B 2090/3784* (2016.02); *A61B 2218/002* (2013.01); *A61M 2025/0042* (2013.01); *A61M 2025/0092* (2013.01); *A61M 2025/1047* (2013.01)

(58) Field of Classification Search
CPC . A61B 5/6859; A61B 5/6868; A61B 18/1492; A61N 1/0534; A61N 1/36067; A61N 1/36082
See application file for complete search history.

(56) References Cited

U.S. PATENT DOCUMENTS

| | | | |
|---|---|---|---|
| 4,774,949 A | 10/1988 | Fogarty | |
| 5,464,395 A | 11/1995 | Faxon et al. | |
| 5,507,743 A * | 4/1996 | Edwards | A61B 18/1815 |
| | | | 600/373 |
| 6,068,638 A | 5/2000 | Makower | |
| 6,190,353 B1 | 2/2001 | Makower et al. | |
| 6,217,527 B1 * | 4/2001 | Selmon | A61B 17/3207 |
| | | | 604/164.11 |
| 6,293,951 B1 | 9/2001 | Alferness et al. | |
| 6,458,098 B1 * | 10/2002 | Kanesaka | A61M 25/0084 |
| | | | 607/101 |
| 6,491,707 B2 | 12/2002 | Makower et al. | |
| 6,511,458 B2 | 1/2003 | Milo et al. | |
| 6,544,230 B1 | 4/2003 | Flaherty et al. | |
| 6,602,241 B2 | 8/2003 | Makower et al. | |
| 6,660,024 B1 | 12/2003 | Flaherty et al. | |
| 6,669,687 B1 | 12/2003 | Saadat | |
| 6,685,716 B1 | 2/2004 | Flaherty et al. | |
| 6,692,466 B1 | 2/2004 | Chow et al. | |
| 6,694,983 B2 | 2/2004 | Wolf et al. | |
| 6,709,444 B1 | 3/2004 | Makower | |
| 6,726,677 B1 * | 4/2004 | Flaherty | A61B 17/3417 |
| | | | 604/528 |
| 7,141,041 B2 | 11/2006 | Seward | |
| 7,273,469 B1 | 9/2007 | Chan et al. | |
| 8,483,794 B2 | 7/2013 | Williams et al. | |
| 8,636,715 B2 * | 1/2014 | Patel | A61M 25/0084 |
| | | | 604/529 |
| 8,721,590 B2 | 5/2014 | Seward et al. | |
| 8,753,366 B2 | 6/2014 | Makower et al. | |
| 9,220,874 B2 | 12/2015 | Pillai et al. | |
| 9,511,214 B2 | 12/2016 | Pillai | |
| 9,877,833 B1 | 1/2018 | Bishop et al. | |
| 10,124,195 B2 | 11/2018 | Zarins et al. | |
| 10,219,855 B2 | 3/2019 | Gelfand et al. | |
| 10,264,987 B2 | 4/2019 | Imran | |
| 10,307,576 B2 | 6/2019 | Heilman et al. | |
| 2002/0002349 A1 | 1/2002 | Flaherty et al. | |
| 2002/0198512 A1 | 12/2002 | Seward | |
| 2003/0236494 A1 | 12/2003 | Seward | |
| 2004/0138643 A1 | 7/2004 | Seward et al. | |
| 2005/0137647 A1 | 6/2005 | Wallace et al. | |
| 2008/0051756 A1 | 2/2008 | Makower et al. | |
| 2009/0142306 A1 | 6/2009 | Seward et al. | |
| 2009/0222083 A1 | 9/2009 | Nguyen et al. | |
| 2010/0185172 A1 | 7/2010 | Fabro | |
| 2010/0198297 A1 | 8/2010 | Cogan et al. | |
| 2010/0211131 A1 | 8/2010 | Williams et al. | |
| 2010/0249491 A1 | 9/2010 | Farnan et al. | |
| 2012/0053485 A1 * | 3/2012 | Bloom | A61M 25/1002 |
| | | | 600/104 |
| 2012/0136247 A1 | 5/2012 | Pillai | |
| 2013/0103026 A1 * | 4/2013 | Kleshinski | A61B 18/1492 |
| | | | 606/41 |
| 2013/0245430 A1 | 9/2013 | Selmon et al. | |
| 2013/0245533 A1 | 9/2013 | Kahn et al. | |
| 2013/0252932 A1 | 9/2013 | Seward | |
| 2014/0121749 A1 | 5/2014 | Roeder | |
| 2014/0378906 A1 | 12/2014 | Fischell et al. | |
| 2015/0005763 A1 * | 1/2015 | Klink | A61B 18/1492 |
| | | | 606/41 |
| 2015/0141836 A1 | 5/2015 | Naumann et al. | |
| 2015/0141959 A1 | 5/2015 | Seward | |
| 2015/0224289 A1 | 8/2015 | Seward | |
| 2016/0193459 A1 | 7/2016 | Gaudiani | |
| 2016/0243333 A1 | 8/2016 | Seward | |
| 2016/0374710 A1 | 12/2016 | Sinelnikov et al. | |
| 2017/0157375 A1 | 6/2017 | Heilman | |
| 2017/0231563 A1 | 8/2017 | Tsamir et al. | |
| 2017/0246427 A1 * | 8/2017 | Gurley | A61B 17/22 |
| 2018/0161550 A1 | 6/2018 | Pillai et al. | |
| 2018/0161551 A1 | 6/2018 | Pillai | |
| 2018/0169075 A1 | 6/2018 | Seward | |
| 2018/0193593 A1 | 7/2018 | Seward et al. | |
| 2018/0353488 A1 | 12/2018 | Seward | |
| 2019/0008580 A1 * | 1/2019 | Fischell | A61B 17/320068 |
| 2019/0038438 A1 | 2/2019 | John et al. | |
| 2019/0134349 A1 | 5/2019 | Cohn et al. | |
| 2019/0105477 A1 | 6/2019 | Heilman et al. | |
| 2020/0094028 A1 | 3/2020 | Seward | |
| 2020/0375766 A1 | 12/2020 | Malek | |
| 2020/0406018 A1 | 12/2020 | Malek et al. | |
| 2021/0361950 A1 | 11/2021 | Opie et al. | |
| 2022/0361743 A1 | 11/2022 | Chan et al. | |

OTHER PUBLICATIONS

"Ultrathin needle can deliver drugs directly to the brain" MIT News, https://news.mit.edu/2018/ultrathin-needle-can-deliver-drugs-directly-brain-0124 dated Jan. 24, 2018 (6 pages).

Dhanasingh A, Jolly C, "An overview of cochlear implant electrode array designs," Hearing Research (2017) 356:93-103 www.elsevier.com/locate/heares.

Brilakis E. et al. "Guiding Principles for Chronic Total Occlusion Percutaneous Coronary Intervention: A Global Expert Consensus Document" Circulation 140: 420-433 (2019).

* cited by examiner

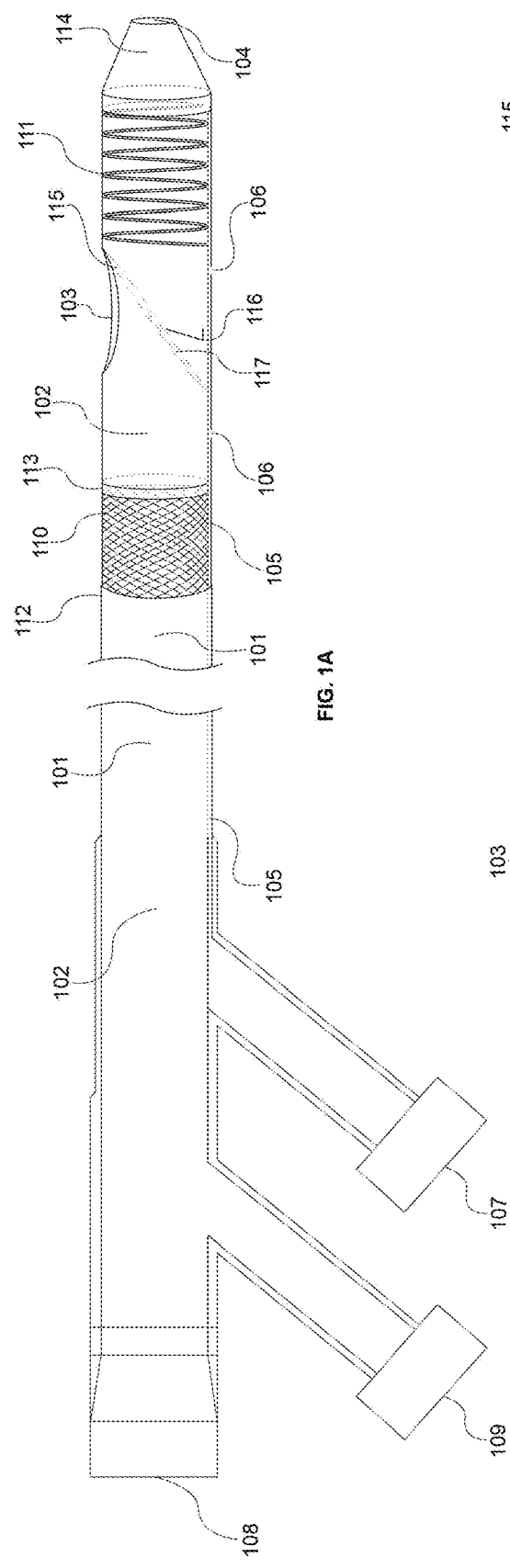
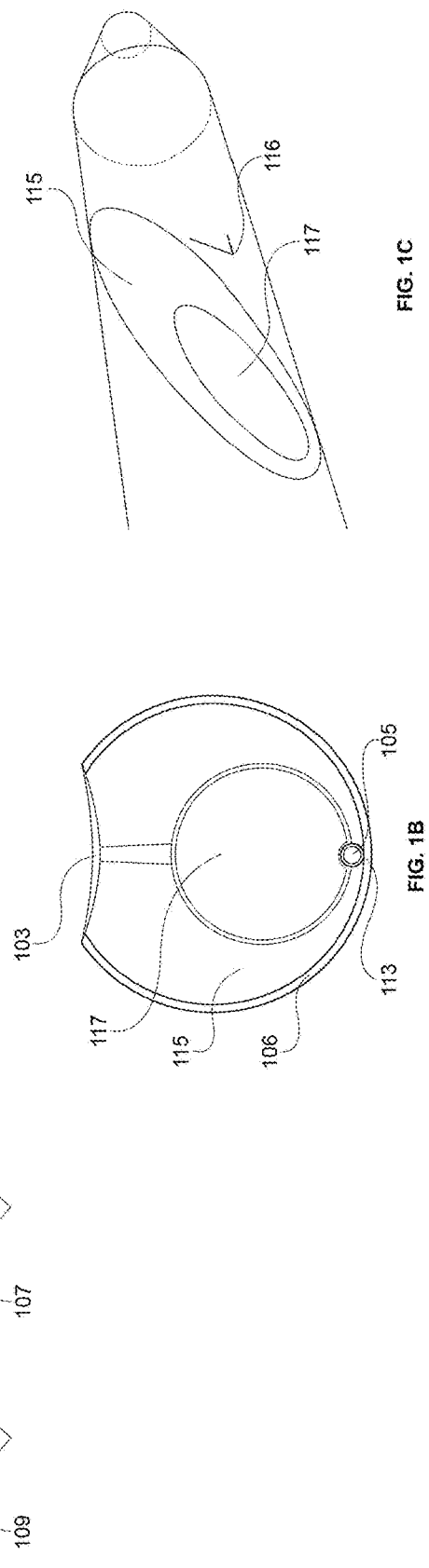
FIG. 1A
FIG. 1B
FIG. 1C

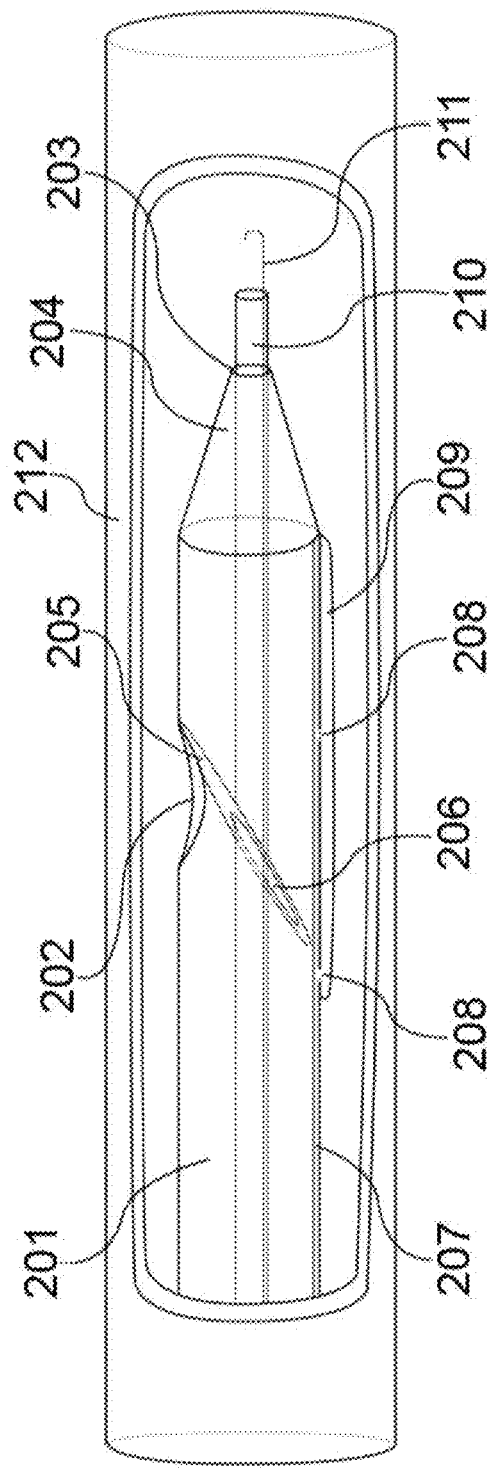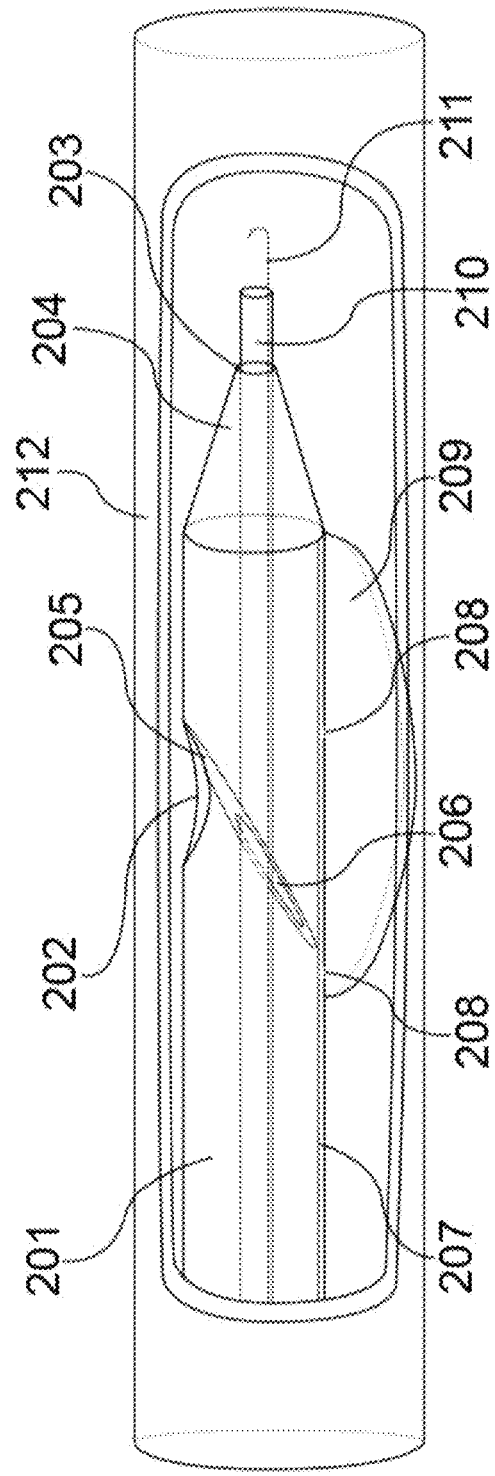
FIG. 2A
FIG. 2B

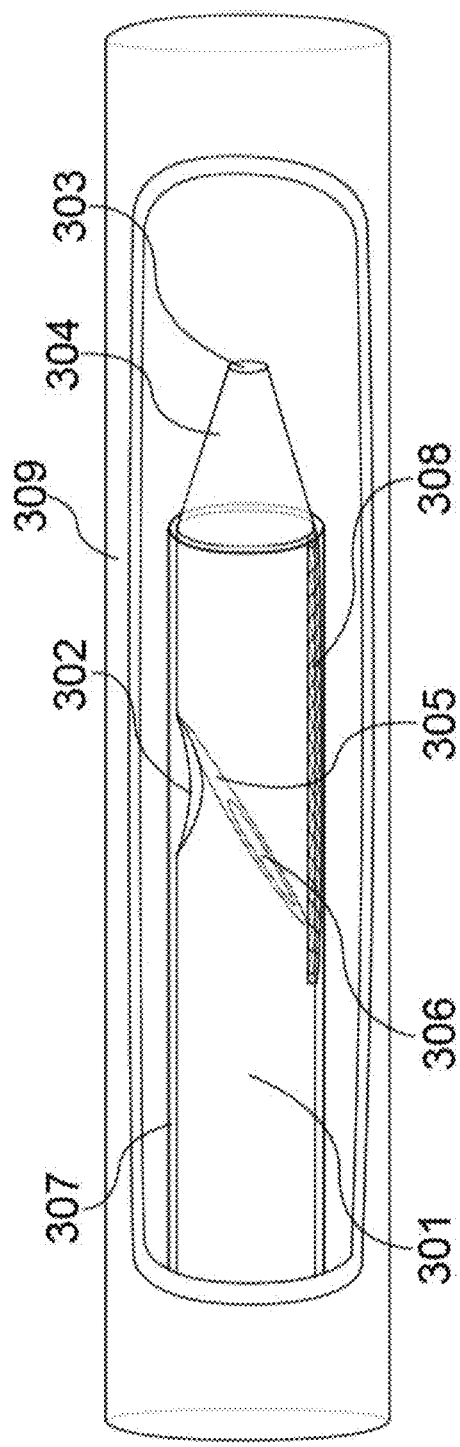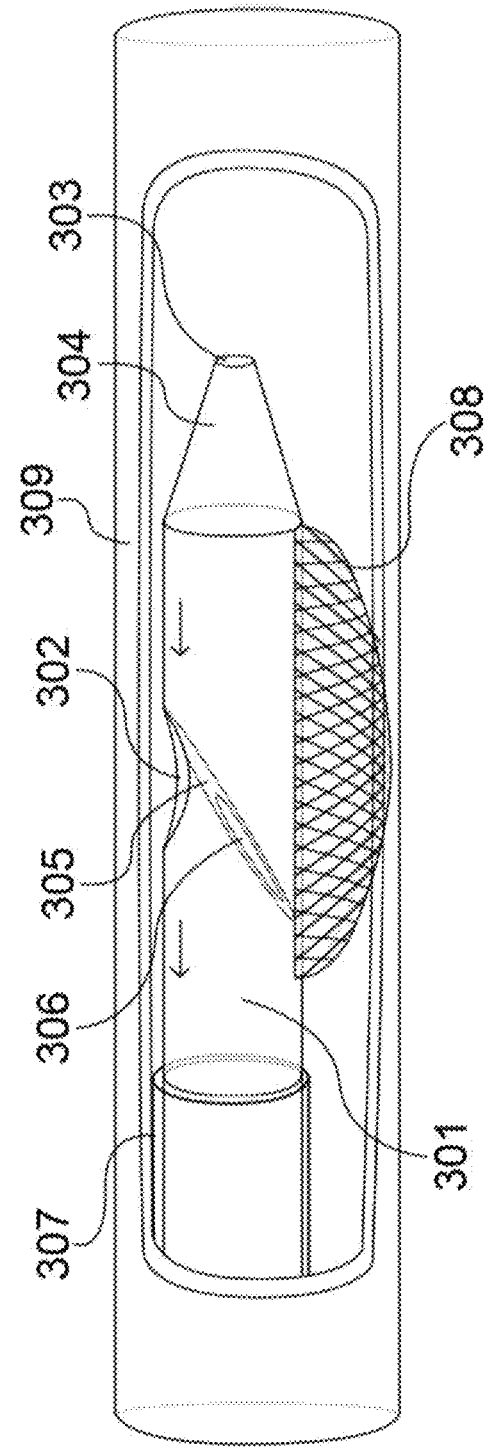
FIG. 3A
FIG. 3B

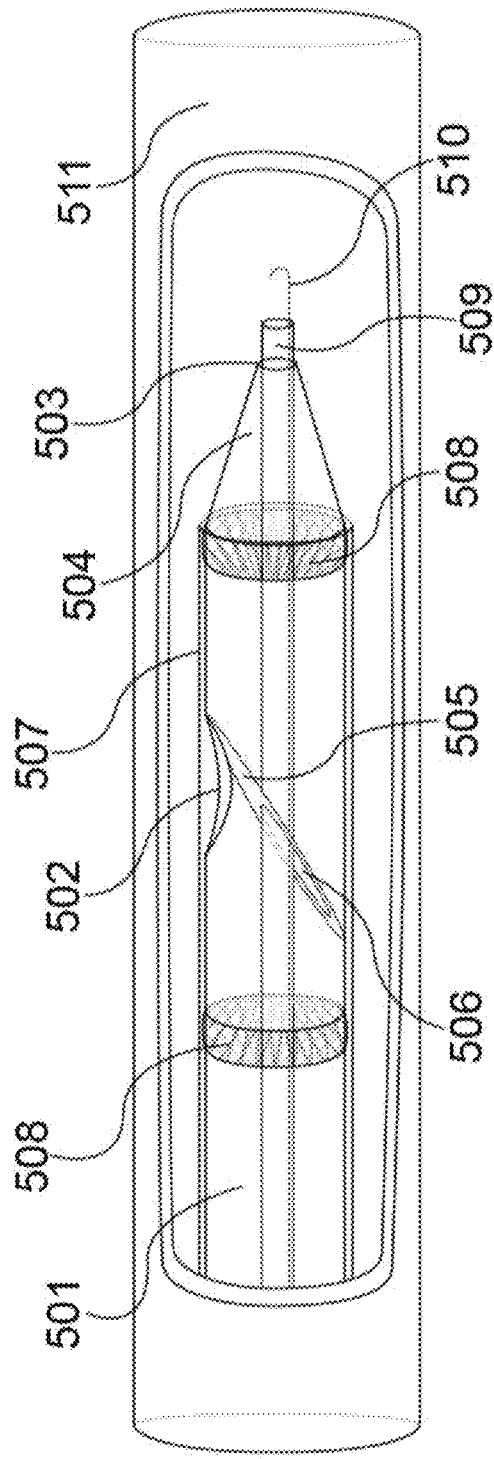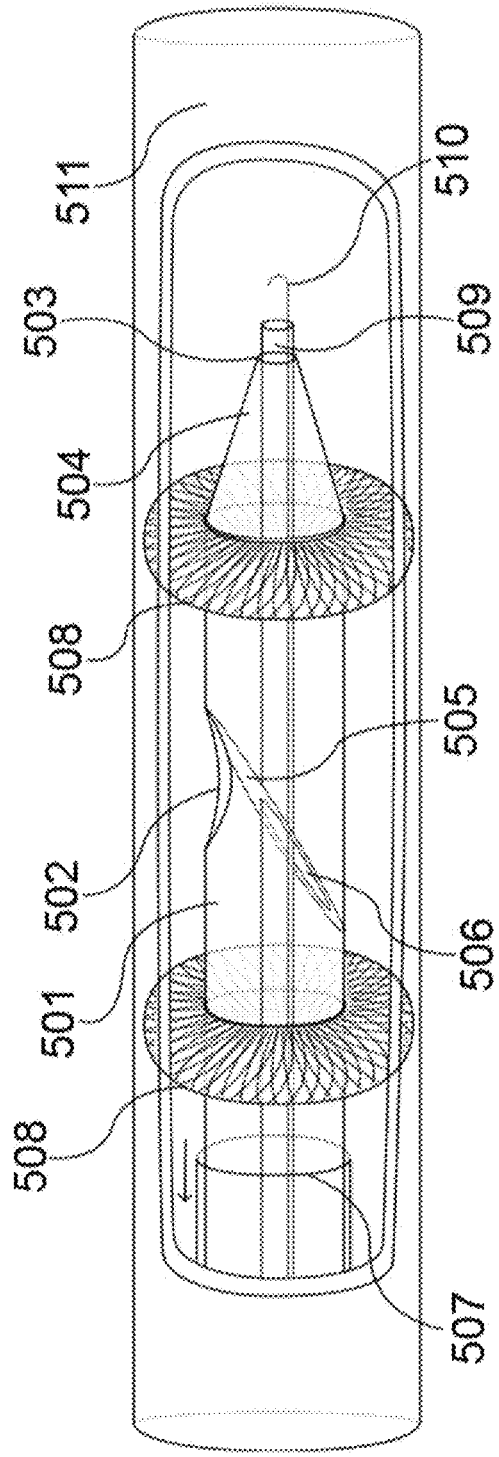
FIG. 5A
FIG. 5B

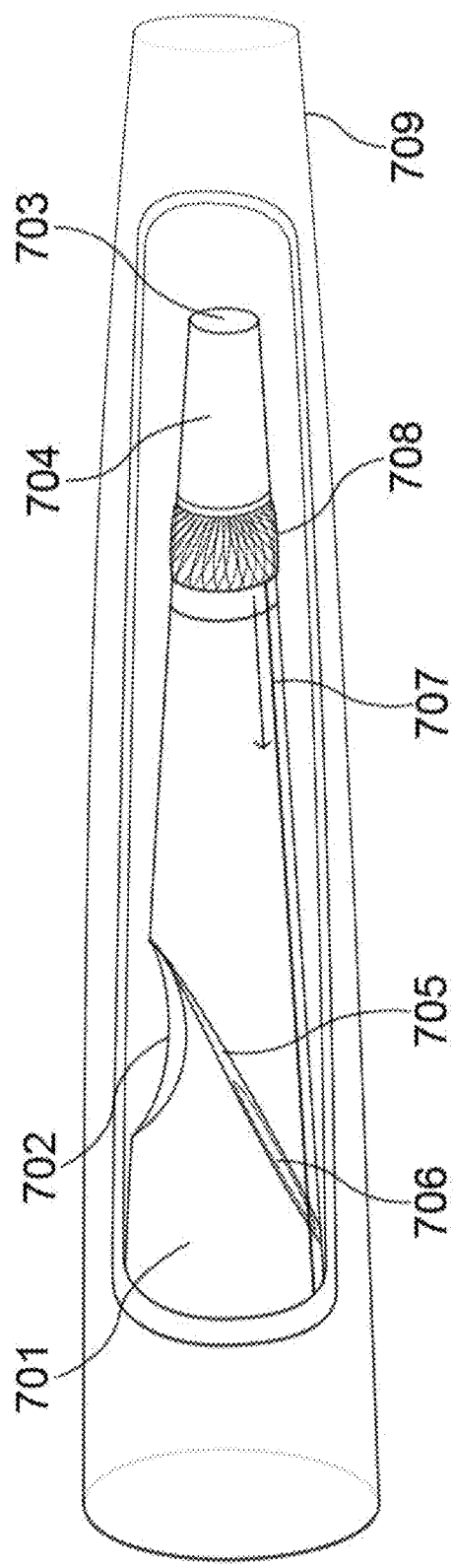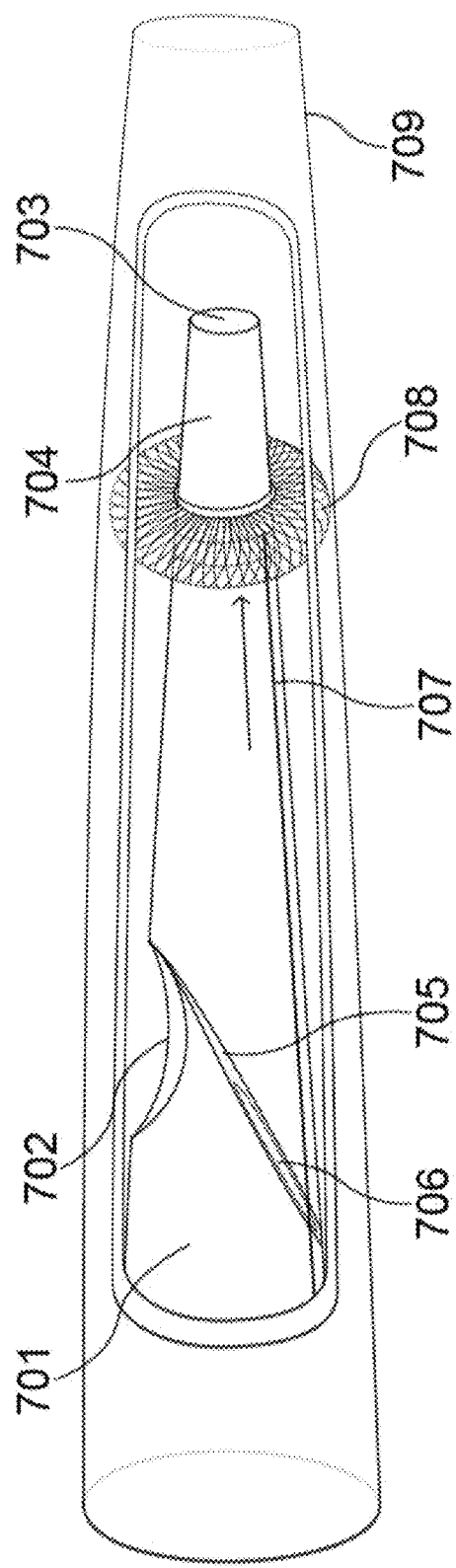

APPARATUS, SYSTEMS AND METHODS FOR TRANSVASCULAR ACCESS TO THE BRAIN

INCORPORATION BY REFERENCE TO ANY PRIORITY APPLICATIONS

This application is a continuation of U.S. patent application Ser. No. 17/956,382, filed on Sep. 29, 2022, which is a continuation of U.S. patent application Ser. No. 17/624,225, filed on Dec. 30, 2021, now U.S. Pat. No. 11,497,552, which is a U.S. National Stage patent application for PCT application no. PCT/US2020/041246, filed on Jul. 8, 2020, which claims the benefit of priority to U.S. Provisional Application No. 62/871,976, filed on Jul. 9, 2019, all of which are incorporated by reference in their entirety herein for all purposes. Priority is claimed pursuant to 35 U.S.C. § 120 and 35 U.S.C. § 119.

TECHNICAL FIELD

The present disclosure is directed towards a device, and related systems and methods for transvascular access to extravascular spaces, particularly the brain, intracranial structures, and/or the subdural or subarachnoid spaces.

BACKGROUND

Access to brain tissue may be required to confirm or treat neurologic diseases involving malignancy, inflammation, aberrant circuitry, or neuropathology in general, as well as to investigate fundamental properties of the brain for basic science exploration. Access to samples of intracranial tissue (i.e., for biopsy, in situ imaging, or cytological analysis) can be used to provide prognosis, tailor treatments, and monitor responses to treatment, as well as advance scientific understanding of the brain and its related functions or physiology. In addition to being used for evaluation via methods of histology, in situ imaging, and cytology, access to regions of brain tissue may be useful for the insertion of devices, such as probes, drug delivery systems or apparatuses, electronic devices with tissue or media sensing/stimulating/modulating properties (e.g., deep brain stimulators, optoelectronic devices, electrode-based microfluidic devices, cortical/intracortical arrays, or other forms of closed-loop neuromodulatory systems), or therapeutic agents (e.g., thermal ablative energy or chemicals, chemotherapeutics, immunonologics, or cytoactive agents that either do not readily cross the blood brain barrier, selectively target cell-populations of interest, or may cause excessive systemic toxicity).

Conventional methods for accessing brain tissue are invasive as they require open craniotomy and/or stereotactic surgery through burr holes. Consequently, conventional methods of accessing brain tissue are prone to the complications of surgery. Complications include disfigurement, pain, perioperative infection, symptomatic hemorrhage, seizure, edema, skull and dura defects, increased length of hospital stay, patient fear/anxiety, morbidity tolerance, hospital admissions associated with high costs and significant rates of complications, neurologic deficits, and even death. Accordingly, the threshold for neurosurgical intervention remains high due to either risks or physician/patient reluctance, which may in turn result in delays to diagnosis, treatment, and consequently, worse outcomes.

Further, conventional methods for accessing brain tissue may rely upon stereotactic neurosurgical methods with proxy fiducial markers, which may result in mistargeting, suboptimal placement, or excessive collateral damage. Stereotactic neurosurgery may rely upon static or temporally irresolute non-invasive imaging (e.g., pre-operative magnetic resonance imaging (MRI) and/or co-registration with non-invasive imaging modalities, linear/line-of-sight trajectories, and external fiducial markers to guide tissue biopsy, ablative therapies, electrode placement, and device implantation. The trajectories of endoscopic instrumentation in stereotactic neurosurgery rely on optimal burr hole drilling technique/execution and/or the fidelity of external fiducial markers and/or the accuracy of static or temporally irresolute image references. However, fiducial markers may physically move during the pre-operative or intraoperative period. and are located at a distance from the target tissue, which may result in suboptimal targeting when there are minor deviations in the incident insertion angle. These and more invasive methods may rely upon removing a cortical bone, dissection or incision of the meninges, and gross manipulation of the brain either by retraction, resection, suction, or ablation of tissue regions of interest. The large and rigid instrumentation (e.g., endoscopes, cannulas, etc.) utilized in minimally invasive stereotactic neurosurgery relies on linear or line-of-sight trajectories to reach a target region of interest, resulting in excessive and unwanted collateral damage, which is often a source of iatrogenic harm.

Minimally invasive catheter-based approaches to medical intervention are experiencing rising demand due to preference by clinicians and patients alike, and recognition by payers of the potential cost-savings to the healthcare system. Since their inception, percutaneous catheter-based interventions have lowered the threshold and broadened the inclusion criteria for diagnosing and treating disease earlier in its course and in patients with advanced disease or otherwise deemed too high risk for standard surgical or more invasive percutaneous approaches. Moreover, percutaneous catheter-based endovascular methods of diagnosis and treatment continue to evolve with increasing sophistication due to advances in materials science, nano- and micro-fabrication methods, optical technology, microelectromechanical systems, and engineering that often compare to, or in many cases supplant, open and current state of the art minimally invasive surgical approaches without compromising efficacy. Despite these technological advancements, catheter-based neuroendovascular modes of diagnosis and treatment for non-vascular disease remain under-developed.

In humans, the cerebral venous system courses through and overlays a range of important brain structures and provide access to a number of functionally significant cortical and subcortical structures and represents a promising avenue for biopsy, ablation, targeted drug delivery, epilepsy mapping, neuronal recording, neurostimulation, neuromodulation, and brain-machine interface. Specifically, the Superior Sagittal Sinus, the Inferior Anastomotic Vein of Labbé, the Superior Anastomotic Vein of Trolard, Superficial Middle Cerebral Vein, Superior Petrosal Sinus, Great Vein of Galen, Internal Cerebral Veins, and the Basal Vein of Rosenthal, and their respective tributaries provide endovascular routes to the limbic structures, thalamus, basal ganglia, occipital, temporal, parietal, and frontal cortices. The diameters of the Superior Sagittal Sinus, Transverse Sinus, and Straight Sinus in humans are reported to measure between 3.0 mm to 4.5 mm, 2.0 to 4.0 mm, and 1.5 to 3.0 mm (rostral to caudal), respectively. The Anastomotic Vein of Labbé ranges between 2.6 mm to ~3 mm. The deep cerebral venous system—namely, the Great Vein of Galen, Basal Vein of Rosenthal, and internal cerebral veins— features rostral to caudal diameter ranges of 1.84 mm to 2.32 mm, 1.72 mm to 1.78 mm, and 0.90 mm to 1.60 mm, respectively. Advantageously, the cerebral venous system is a low flow system with pressures ranging between 10-15 mm Hg. Compared to the arterial system, cerebral veins possess relatively large lumens due to a negligible tunica media. These low flow vessels represent a promising avenue for transvascular access to extravascular spaces in the intracranial vault with the proposed transvascular catheter-based approach.

Techniques for navigating the subarachnoid space in human cadaveric brain did so with endoscopes and microcatheters from a percutaneous translumbar intraspinal route. These methods demonstrated atraumatic catheter navigation through the subarachnoid space as far as the anterior fossa from a lumbar puncture site using a passive-traction, over-the-wire technique. Notably, these conventional techniques do not provide a method for introducing endovascular catheters through systemic or extracranial vessels, advancing endovascular catheter(s) through an anastomotic vascular channel to gain access to the intracranial vascular system, or exiting an intracranial vascular tubular lumen via transvascular puncture to then enter and navigate extravascular spaces within the intracranial vault.

Conventional techniques for transvenous access from the inferior petrosal sinus (IPS) into cerebellar-pontine angle cistern describe the use a of needle encased in a sheathing component navigated over a flat rail guidewire affixed to a temporary stent. When unsheathed, the needle penetrates across the vessel lumen and the encasing dura of the IPS for subsequent placement of a catheter-deliverable transvenous/transdural cerebrospinal fluid shunt. The implanted shunt will have its distal end residing in the cerebellopontine angle cistern (CPA cistern) and its more proximal component within the IPS lumen.

As alluded to above, these conventional techniques stabilize transcatheter device delivery systems with the deployment of a temporary stent distal to the intended transvenous puncture site to anchor a flat rail guidewire over which the sheathed needle is tracked. Importantly, these conventional techniques rely on and exploit the anatomical configuration and angle of the IPS near the CPA cistern. These conventional techniques however are not configured for distal venous access beyond the sigmoid sinus into more distal cerebral veins/sinuses nor are these instruments or techniques configured to navigate to remote extravascular spaces or tissue beyond the perivascular CPA cisternal space (i.e., to/through/within brain parenchyma, or the subdural/subarachnoid compartments), nor are these prior art techniques configured to provide maneuvers, tools, or materials for ensuring hemostasis after transvascular puncture and the removal of the select transvascular instrumentation, devices, or tools proposed herein. Pertinently, these conventional techniques solely provide a method for implanting and explanting a device or delivering therapeutics into the CPA cistern from the IPS.

Conventional methods for implantation of an intravascular electrode array within a tubular lumen (i.e., intracranial vessel) and configuring it to operate with a tissue/media signal sense or stimulate system and related components do not describe a method for extravascular navigation of the intracranial vault nor do these conventional methods describe directly sampling or accessing brain tissue for biopsy, imaging, ablation, or drug delivery.

In addition, conventional methods for recording or stimulating may only sense or stimulate tissue or media located in close (2-5 millimeters) proximity to the blood vessel wherein it is implanted and are not configured to interface directly with the tissue topology over a spatial extent to capture the source, spatiotemporal evolution, or dynamics of biopotential signals originating from the cortical surface across a centimeter scale and/or across cytoarchitectonic boundaries, such as the proposed embodied method would enable.

Furthermore, conventional systems demonstrating transvenous deep brain stimulator insertion do not detail the requisite catheter scale, specifications, or co-axial transcatheter instrumentation, nor do they describe methods or devices for ensuring post-procedural hemostasis, such as those described herein. Prior-work describing remote navigation to distal cerebral veins for electrophysiology capture and/or radiofrequency ablation are maintained intraluminally and do not provide the in situ, topological precision necessary for clinical applications, such as epilepsy, cortical mapping/stimulation, biopsy, in situ imaging, thermal energy ablation, or direct drug delivery.

Conventional systems featuring a catheter design with serially placed balloons have a plurality of lateral wall ports for concentrating embolic or chemotherapeutic agents within a vessel segment of interest to concentrate cytoactive agents for improved transmural diffusion to an extravascular tissue segment of interest. These conventional methods do not allow nor are they configured for co-axial or transcatheter instrumentation through these lateral ports. Conventional systems utilizing serially placed balloons at the distal end of a catheter have been described to occlude transcutaneous stomas or lumens of the gastrointestinal and genitourinary tracts, but are not configured with the requisite scale, materials, nor are previously discussed methods configured for endovascular use, for intracranial navigation, nor do they permit co-axial or transcatheter instrumentation from a lateral wall working exit lumen port.

Conventional catheters used for the uterus and pelvis are also limited in that they are typically made of silicon, or with other mechanically weak materials that are susceptible to breakage.

Conventional systems with lateral wall or offset exit ports featuring deployable needles or guidewires through those ports have been illustrated for use to cross chronic total occlusions (CTOs) or for enabling biopsy of the myocardial tissue. These conventional systems are configured for accessing the subintimal or perivascular tissue or media from the lumen of peripheral and coronary arteries. More particularly, commercially-available embodiments of conventional systems for CTOs have a stiff segment at their distal end, and are configured to provide distal pushability across stenotic or occluded segments of peripheral arteries, and are not configured for atraumatically navigating the intracranial cerebral venous system. Conventional systems for transluminal interventions using vessel wall penetrators, required a multi-lumen design and were limited to operation in high pressure vessels.

SUMMARY

The present disclosure is directed towards a guide/access catheter device, and related systems and methods for transvenous access and subdural navigation to extravascular regions of interest in the extra-axial and intra-axial compartments of the brain, including subdural or subarachnoid spaces, and tissue parenchyma. The devices disclosed herein pertain to endovascular guide/access catheters, co-axially-introduced transcatheter instruments, and transvascularly navigated catheters for transcatheter device delivery or deployment, implantation, and drug delivery directly to extra-vascular intracranial structures, tissues, media, and components for the evaluation, diagnosis, and treatment of neurologic disease and disorders. In some embodiments, the device may be used for targeted tissue biopsy of, in situ imaging of, device delivery to, device implantation into, or direct drug delivery to intracranial structures, such as the brain parenchyma, subdural or subarachnoid space.

Described herein is a catheter-based endovascular transvenous approach and apparatus for directly accessing the brain and its constituent components. The present invention relates to a variety of methods and devices to enable transvascular, more particularly transvenous, access to the subdural space, subarachnoid space, and brain parenchyma with catheters and catheter-related or delivered devices with a selective deflector for the diagnosis and treatment of seizure disorder, brain cancer, infection, inflammation, degeneration, psychiatric disease, memory or motor impairment, and movement disorder.

The endovascular catheter proposed herein can be made from a specific set of polymers and reinforcement materials embedded within the walls of the catheter (such as metal alloys configured in braided or coiled patterns, varying weave density (pitch per inch), etc.) to confer an optimal combination of flexibility, tensile strength, torque, steerability, trackability, pushability, and compression/kink resistance. Endovascular catheters, unlike catheters used in stomas or through avascular tubular structures, must be thin-walled yet confer a balance between high tensile strength, burst resistance, compression resistance, and flexibility. The endovascular catheters disclosed herein have superior biocompatibility, are biologically inert (i.e., do not promote an inflammatory response), are preferably coated with hydrophilic or lubricous materials to prevent thrombogenicity, and are nonmutagenic (non-toxic and do not contain leachable additives that could be cytotoxic or lead to systemic toxicity) and resist biofilm formation.

The systems and methods described herein are capable for use in low-pressure environments. For example, embodiments disclosed herein are intended for use in the cerebral veins (low pressure) for positioning, anchoring, and supporting subsequently introduced catheters and related instrumentation intended for navigating the subdural/subarachnoid space, as well as for buttressing the back propagation of forward insertion forces. Further, the present invention maintains a wide diameter lumen from the proximal end of the catheter through to the lateral wall working exit lumen port where co-axial catheters may be deployed. This is in contrast to conventional systems in which were tailored for use in peripheral arterial systems and their lateral wall working exit lumen ports feature relatively small diameters allowing only for deployment of thin penetrators or guidewires.

Further, the disclosed embodiments, utilize advancements, such as low-profile monolithic tubing constructs, catheters with steerability, flexible/steerable needles, and submillimeter needle-/catheter-based fiber optic photonic or sonographic imaging apparatuses, catheter-deliverable super-elastic highly compressible shape memory materials or devices, wireless energy transfer/charge (e.g., near-field radiofrequency), solid-state micro-batteries, piezo-/triboelectric energy harvesting methods, injectable flexible biocompatible polymeric thin film or mesh electronics, and ultracompact circuit designs (e.g., CMOS, ASIC, etc.) provide distinct advantages to conventional systems which were not capable for use in connection with minimally invasive transvascular methods and devices for the diagnosis and treatment of neurologic disease and disorders as is described herein. The proposed methods disclosed herein would enable improved distal navigation through tortuous vessels, controlled transvascular access, in-situ imaging, untethered implantable devices featuring wireless energy transfer (e.g., near field/energy-harvesting) or high bandwidth data transmission capabilities, as well as catheter delivery of appropriately-scaled and/or biologically compatible medical devices (e.g., cyto-compatible compressible shape memory alloys/materials) through relatively small bore (2-6 Fr) catheters with equal or superior efficacy to conventional systems requiring invasive neurosurgery mediated primarily through burr holes or craniotomy.

In some embodiments, an access catheter system is used for extravascular procedures in the brain. The access catheter may include an elongate, flexible tubular body, having a proximal end, a distal end and at least one lumen extending axially there through, a side exit port positioned along the elongate, flexible tubular body, spaced proximally apart from the distal end and in communication with the lumen, a distal end port in communication with the lumen proximate the distal end, and a selective deflector positioned within the lumen, wherein the selective deflector is configured to deflect a procedure catheter having a diameter greater than a preset threshold out through the side exit port, and wherein the selective deflector is configured to permit a guide catheter having a diameter of less than the preset threshold to pass distally beyond the deflector and out through the distal end port.

Optionally, the selective deflector may include an inclined barrier positioned within and partially occluding the lumen. In some embodiments, the inclined barrier includes an aperture and the aperture diameter may be less than a side exit port diameter of the side exit port. The access catheter system may also include a laterally expandable support carried by the elongate, flexible tubular body, and the laterally expandable support may be positioned on an opposite side of the tubular body from the side exit port. Optionally, the laterally expandable support may include an inflatable balloon. Optionally, the laterally expandable support may include at least one laterally deflectable strut. The access catheter system may include a first occlusion balloon and a second occlusion balloon, wherein the first occlusion balloon is positioned on the tubular body on a proximal side of the side exit port and the second occlusion balloon is positioned on the tubular body on a distal side of the side exit port.

Optionally, the procedure catheter may include at least one of a flexible needle, a steerable needle, a retractable needle sheath, a retractable guard, a dilator, a steerable catheter, an imaging device, an ablation device, force sensors, temperature sensors, biopsy device, a compressible-expandable biopotential sensing or stimulation device or implant, a convection-enhanced drug delivery microcatheter, or an injectable drug eluting bioresorbable nanofluidic implant. The ablation device or the imaging device may include a microelectronic mechanical system, optical technology, a flexible laser-cut hypotube, or co-axial actuating mechanical system. The compressible-expandable biopotential sensing or stimulation device or implant may include a shape memory scaffold embedded with electrodes configured to transmit to a connector for recoding neurons, mapping cortical activity, stimulating neurons, or modulating cortical activity.

In some embodiments, a method of providing transvascular access to an extravascular access site in a vessel may include the steps of advancing an access catheter over a guide to position a side exit port of the access catheter adjacent to a target site of the vessel, retracting the guide from the access catheter, and advancing a procedure catheter through the access catheter and to the target side of the vessel via the side exit port of the access catheter, wherein a selective deflector in the access catheter deflects the procedure catheter out through the side exit port, but permits the guide to advance distally beyond the deflector and out of a distal end of the access catheter.

Optionally, advancing the access catheter over the guide may include advancing the access catheter over a microcatheter or guidewire. Optionally, the vessel may include a vein. Optionally, the access catheter may be anchored to the target site by deploying expandable structural members of the access catheter.

Optionally, the method of providing transvascular access may also include the steps of deploying a procedure catheter or instrument through the side exit port, advancing a second device across the vein and into the target area, thereby creating a venous puncture site, advancing a wire through the second device into the target area to deploy a second procedure catheter with advanced functionality, removing the second device, and deploying supporting expandable structural elements of the access catheter.

In some embodiments, the second procedure catheter with advanced functionality may be configured to at least one of collect or deliver media and tissue, locally image tissue, deliver materials, drugs, or compounds, implant devices, record from neurons, modulate neuronal activity, or ablate tissue. Optionally, deploying supporting expandable structural elements of the access catheter may include the steps of repositioning the access catheter such that at least one balloon of the access catheter overlays the venous puncture site, inflating at least one balloon of the access catheter such that it contacts the venous puncture site, thereby tamponades the venous puncture site to produce hemostasis, evaluating if hemostasis has been achieved by deflating the at least one balloon of the access catheter, and deploying an implantable biosynthetic, bioabsorbable hemostatic material from the side exit port responsive to determining that hemostasis from balloon tamponade not being achieved. In some embodiments, the biosynthetic, bioabsorbable hemostatic material includes at least one of Poly (L) polymer, and Dextran-Sucrose-Sodium Citrate polymer.

BRIEF DESCRIPTION

The drawings illustrate the design and utility of embodiment(s) of the present disclosure, in which similar elements are referred to by common reference numerals. In order to better appreciate the advantages and objects of the present disclosure, reference should be made to the accompanying drawings that illustrate the embodiment(s). The drawings, however, depict the embodiment(s) of the disclosure, and should not be taken as limiting its scope. The embodiment(s) of the disclosure will be described and explained with additional specificity and detail through the use of the accompanying drawings in which:

FIG. 1A illustrates a schematic diagram of the access catheter device in accordance with embodiments of the present disclosure.

FIG. 1B illustrates a cross-sectional view of the access catheter device of FIG. 1A in accordance with embodiments of the present disclosure.

FIG. 1C illustrates a second cross-sectional view of the access catheter device of FIGS. 1A and 1B in accordance with embodiments of the present disclosure.

FIG. 2A illustrates an embodiment of an access catheter device featuring an inflatable elastomeric balloon in a first state in accordance with some embodiments of the present disclosure.

FIG. 2B illustrates an embodiment of an access catheter device featuring an inflatable elastomeric balloon of FIG. 2A in a second state in accordance with some embodiments of the present disclosure.

FIG. 3A illustrates an embodiment of an access/guide catheter device featuring a compressible-expandable offset non-occlusive structural element/member in a first state in accordance with some embodiments of the present disclosure.

FIG. 3B illustrates an embodiment of an access/guide catheter device featuring the compressible-expandable offset non-occlusive structural element/member of FIG. 3A in a second state in accordance with some embodiments of the present disclosure.

FIG. 5A illustrates an embodiment of an access catheter device featuring two serially placed compressible-expandable non-occlusive wire mesh support structures in a first state in accordance with some embodiments of the present disclosure.

FIG. 5B illustrates an embodiment of an access catheter device featuring two serially placed compressible-expandable non-occlusive wire mesh support structures of FIG. 5A in a second state in accordance with some embodiments of the present disclosure.

FIG. 7A illustrates an embodiment of a hybrid-sized catheter device featuring a compressible-expandable non-occlusive wire mesh in first state in accordance with some embodiments of the present disclosure.

FIG. 7B illustrates an embodiment of a hybrid-sized catheter device featuring a compressible-expandable non-occlusive wire mesh of FIG. 7A in a second state in accordance with some embodiments of the present disclosure.

DETAILED DESCRIPTION

Figure 4A:
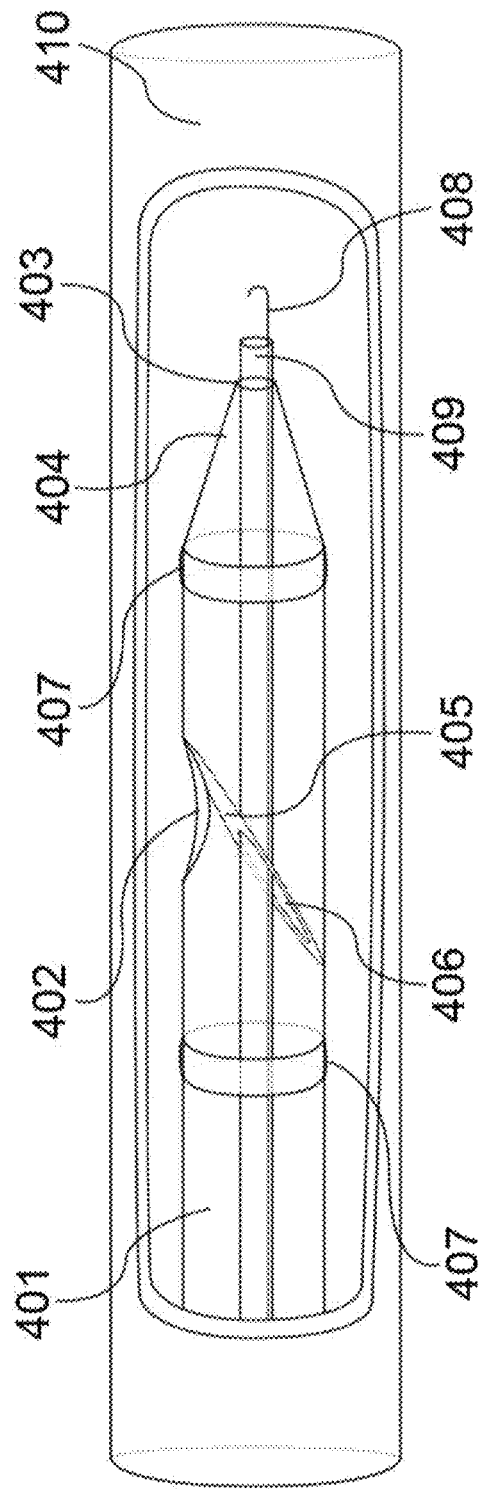
FIG. 4A illustrates an embodiment of an access catheter device featuring inflatable elastomeric double-balloons in a first state in accordance with some embodiments of the present disclosure.

The present disclosure describes a system in which a guide/access catheter provides an endovascular conduit for co-axial catheter systems and transcatheter instrumentation to transvascularly access the subdural space, subarachnoid space, and the brain parenchyma—for targeted device delivery or implantation and/or tissue/media insertion/collection without the needs for burr holes or craniotomy. Various novel neuroendovascular transvenous access/guide catheter designs and a variety of clinical applications that the catheter(s) would enable are described herein, such as for the diagnosis and treatment of seizure disorder, pathologic brain tissue (e.g., cancer s etc.), psychiatric disease, —cognitive/motor impairment, and movement disorder.

FIG. 1A-C illustrates a schematic diagram of the access catheter device comprising tubular structures featuring proximal and distal ends operably connected through lumen(s), cut-away views of various layers and inner components/features, and cross-section views of inner components/features. In particular, FIG. 1A illustrates a schematic diagram of the access catheter device, FIG. 1B illustrates a cross-sectional view of the access catheter device of FIG. 1A, and FIG. 1C illustrates a second cross-sectional view of the access catheter device of FIGS. 1A and 1B.

The access catheter includes catheter shaft 101, a main central lumen 102, lateral wall working exit lumen port 103, a distal end working exit lumen port 104, a segregated balloon inflation lumen 105, inflation ports 106, balloon inflation ports 107, main ports 108, saline irrigation/infusion ports 109, braided reinforcement 110, coiled reinforcement 111, outer jacket of the catheter shaft 112, an inner liner 113, a reflowed/heat shrunk tapered tip 114, a selective deflector or luminal molding 115 with an angle of luminal molding 116, and a selective passageway 117.

The access catheter 101 may be configured for performing extravascular procedures in the brain. The access catheter 101 may include an elongate, flexible tubular body, and have a proximal end spaced apart from a distal end and at least one lumen extending axially there through. The lateral wall working exit lumen port 103 or side exit port may be positioned along a surface of the elongate, flexible tubular body. The distal end working exit lumen port 104 may be positioned approximate the distal end of the flexible tubular body and in communication with the lumen. In some embodiments, the lateral wall working exit lumen port 103 may be in communication with the lumen 102.

Embodiments of the present disclosure include a catheter shaft featuring a proximal main port 108 on its hub for co-axially introducing catheters and related instrumentation operably connected to a central lumen, a proximal saline infusion port 109 operably connected to the central lumen 102, and a proximal balloon inflation port 107 operably connected to a balloon inflation lumen 105 and inflation hole(s). The proximal end of the catheter device and its central lumen 102 are operably connected to lateral wall 103 and distal end 104 working exit lumen ports. An internal molding 115 can serve as a size-limiting selective passageway for co-axial catheter-related instrumentation to facilitate deployment from either the lateral wall working exit lumen port 103 or the distal end working exit lumen port 104. The catheter device throughout its longitudinal extent may feature discrete segments that can have either braided 110 or coiled 111 reinforcement materials or a combination thereof, and a distal reflowed atraumatic tapered tip 114 without reinforcement materials in accordance with an embodiment of the present disclosure.

A selective deflector 115 may be positioned within the lumen 102. The selective deflector 115 may be configured to deflect a procedure catheter having a diameter greater than a preset threshold out through the side exit port 103, and be further configured to permit a guide catheter having a diameter of less than the preset threshold to pass distally beyond the selective deflector and out through the distal end port 104 via the selective passageway 117. In some embodiments, the selective deflector 115 includes an inclined barrier positioned within and partially occluding the lumen. The inclined barrier may include an aperture that has an aperture diameter less than a side exit port diameter of the side exit port. The angle of inclination of the inclined barrier or angle of luminal molding 116 is illustrated in FIG. 1C. Possible range of angles for the angle of luminal molding 116 include a range between 15°-60° from the horizontal plane of the catheter shaft. The embodiments described herein may include a selective deflector 115 having a luminal molding(s) forming a spherical or oblong shape within the inner lumen of the guide/access catheter. The utility of the luminal moldings is to function as a both rail and a size-limiting selective passageway for co-axial catheters and instruments. The luminal moldings can function as a rail for the larger diameter catheters (>0.90 mm) and penetrators co-axially advanced and introduced through the lateral wall or offset working exit lumen port. The luminal moldings can function as a selective passage of smaller diameter instruments (<0.87 mm), such as microcatheters and guidewires, co-axially advanced through to the distal end working exit lumen port beyond the lateral wall working exit lumen port. The passage of smaller bore catheters or microcatheters exiting the distal end of the catheter device can function to facilitate atraumatic distal navigation through tortuous cerebral venous anatomy.

The offset or lateral wall working lumen exit port 103 may be configured for selective catheter and transcatheter device or instrumentation deployment or delivery. An internal set of leaflets or moldings 116 constructed from semi-compliant materials (polymeric, laser-cut metal, or alloy materials) located within the main central lumen 102 of the guide/access catheter having an angle between 10-60 degrees relative to the longitudinal axis of the tubular catheter shaft may function as a rail to selectively guide wider diameter (>0.90 mm) co-axial catheters and instruments with advanced functionality elements through the offset or lateral wall working exit lumen port. Advanced functionality elements may include, but are not limited to flexible needles, biopsy devices, single or multi-mode optical fiber systems, piezoelectric transducers, complementary mixed-oxide sensors, electrodes or compressible-expandable electrode arrays with stimulating or recording capabilities, drug delivery apparatuses/devices, vascular defect repair materials and the like.

The segregated balloon inflation lumen 105, inflation ports 106, balloon inflation ports 107, main ports 108, saline irrigation/infusion ports 109, and the like, may be configured to allow for the separate control via selective inflation or deflation of one or more balloons or expansion or compression of related lateral expandable support elements via welded pull-wires ranging between 0.20-0.35 mm in diameter, positioned eccentrically along or within the main central lumen of the access catheter. The segregated balloon inflation lumen 105 is located eccentrically within the main catheter shaft along its longitudinal extent. The segmented balloon inflation lumen 105 may be connected to its own proximal inflation port 107 and/or a saline-filled syringe or wire pulley system. These allow for independent inflation and/or deflation of balloons or compression and/or expansion of wire mesh cage elements.

Embodiments disclosed herein relate to a catheter device comprising a tubular shaft with a central lumen having an inner diameter, proximal end opening(s) and distal openings. The device may include a selective deflector that selectively facilitates the passage or deployment of catheters, microcatheters, guidewires, transcatheter devices, tools, instrumentation, or implants Further, the access catheter device may have a proximal opening or port operably connected through a central lumen of a tubular shaft to a lateral wall opening or offset working exit lumen port and to a distal end opening or exit port through a selective deflector.

In some embodiments, the disclosed catheter device features a single circumferential extra-axial compliant member located distally on a steeply tapered end of the catheter shaft, and a lateral wall working exit lumen port that is located between about 1 to 20 mm proximal to the distal compliant member located on the distal tapered end of the endovascular catheter shaft. The distal compliant member may be an elastomeric balloon or a compressible/expandable wire mesh. The lateral wall working lumen exit port may be located on the catheter shaft between about 1 to 20 mm from its distal end and be configured to selectively deploy a coaxially-introduced catheter with or without advanced functionality or unique features from its working exit lumen port(s), as well as transcatheter deliverable instruments or devices. Advantageously, a steeply tapered end may be used to facilitate access to and anchoring within a tapering vein, such as the Great Vein of Galen, the internal cerebral veins, or the basal vein.

In each embodiment, there is a selective passageway for a co-axially introduced flexible needle, guidewire, dilator, catheter each providing selective passageway for transvascular catheter and/or transcatheter instrument access to the subdural or subarachnoid space or brain parenchyma for the diagnosis and treatment of seizure disorder, pathologic brain tissue, psychiatric disease, motor impairment, and movement disorder.

Optionally, the catheters 101 may have outer diameter between about 1.3-2.2 mm. Optionally, the working lumen exit port comprises a diameter between about 0.4-1.95 mm. Optionally, the balloon(s) or expandable mesh bonded to the catheter shaft have/has an outer diameter between about 0.8-5 mm. Optionally, the catheter with advanced functionality comprises an outer diameter between about 0.3 mm to 1.95 mm and an inner diameter between about 0.3 mm to 1.92 mm.

The access catheter device 101 can have an outer jacket 112 comprised of a single or multiple durometer thermoplastic polymeric or copolymeric material (e.g., polyamide, polyether, polyurethane, polyimide, etc.). The longitudinal segments of the multi-durometer catheter can vary its stiffness by the relative ratio of co-polymer blocks (e.g., Pebax: polyamide (stiff) versus polyether (soft), etc.). The ratio of the copolymer block composition of the outer jacket 112 at a proximal segment of the catheter shaft can have stiffer properties (i.e., higher durometer) compared to catheter jacket segments located more distally that can have more flexibility (i.e., lower durometer).

Alternatively or in conjunction, the access catheter device 101 can have reinforcing members, such as braided reinforcements 110 or coiled reinforcements 111 such as wires/polymers/alloys or laser-cut metal hypo-tube constructs, arranged variably in segments along the longitudinal extent of the catheter shaft. The material of these reinforcing members can be stainless steel, tungsten, nitinol, liquid crystal polymer, or laser-etched metal (e.g., stainless steel, nitinol, etc.) hypo-tubes. The reinforcing members including the braided reinforcements 110 and/or coiled reinforcements 111 can be embedded between outer and inner polymeric layers referred to as outer jacket and inner lining, respectively, circumferentially arranged around the catheter central lumen(s). Braided reinforcement 110 patterns can use, for example, sixteen wired or threads arranged in a regular braid pattern (one-under-two, over two) or diamond braid pattern (two-under-two, over two) or eight wires or threads in half-load diamond braid pattern (one-under-one, over one).

An alternative or combination reinforcement pattern may include coiled reinforcements 111 such as variable pitch coiling. An alternative or combination reinforcement pattern may include laser-cut metal hypotube(s) (e.g., stainless steel or nitinol). The reinforcing laser cut metal hypotube can have variable stiffness or flexibility properties along discrete longitudinally arranged structural regions, and these properties can depend on the pitch or frequency of the laser-etched perforations (e.g., pitch: 0.006-0.015, respectively).

The braided reinforcements 110, coiled reinforcements 111, or laser-cut hypotube reinforcement members distributed along the longitudinal extent of the catheter device shaft can have variable weave density, pick per inch (PPI), or pitch along specific segments so as to vary relative stiffness (e.g., <250 PPI, <0.1 inch, or >0.006, respectively) or flexibility (e.g., >20 PPI, >0.005 inch, or <0.015, respectively).

Embodiments of the present disclosure include, the catheter shaft may feature a one or more of reinforcement materials (e.g., stainless steel, tungsten, nitinol, or liquid crystal polymer) or patterns, specifically braided or coiled, and/or variable weave density or pitch as illustrated in FIG. 1B. In some embodiments, a longitudinal segment of the catheter proximal to the offset/lateral wall working exit lumen port may be reinforced with a braided 111 pattern of materials embedded between outer 115 and inner 117 lining to increase the tensile strength and torque transmission of the catheter. Longitudinal segments residing at major flexures in the venous anatomy can be reinforced with coils to provide the catheter shaft with flexibility and kink resistance at major stress/flexure points. A longitudinal segment distal to the offset/lateral wall working exit lumen port 103 can be reinforced with coils 113 embedded between an outer jacket 115 and inner lining 117 to maintain distal trackability and optimal navigability through the acute angle bends of the cerebral vasculature. A distal segment can be non-reinforced with heat shrunk polymeric layers for an atraumatic tip. Not depicted here, embodiments of the catheter shaft may be comprised of laser cut stainless steel or nitinol hypo-tube to confer a similar performance profile of torque transmission, pushability, trackability, flexibility, and navigability for use in the cerebral venous system, subdural or subarachnoid spaces.

In some embodiments, the access catheter device 101 can have an inner liner 113 including a hydrophilic polymer (e.g., polytetrafluoroethylene (PTFE), fluorinated ethylene propylene (FEP), high density polyethylene) that is configured to confer lubriciousness and a low coefficient of friction.

The outer jacket 112 or inner liner 113 of the access catheter 101 may be composed of the same or different polymeric materials and coated with hydrophilic materials. Discreet segments of the access catheter device 101 residing at acute bends can preferably be comprised of coil reinforcement elements or high pitch laser etched metal hypotube reinforcement elements to optimize the kink or compression resistance of the catheter shaft, while at the same time retaining flexibility at known major stress points of vascular tortuosity. Major stress points of vascular tortuosity include, but are not limited to, the junction of the brachiocephalic vein and internal jugular vein, the junction of the internal jugular vein and the sigmoid sinus, and the junction of the transverse sinus and superior sagittal sinus, which is also referred to as the torcular herophili. For example, in some embodiments, the distal end of the access catheter 101 shaft beyond the lateral wall working exit lumen port 103 or side exit, may include a coil reinforced segment for added flexibility with retained trackability to optimize its navigability through tortuous vascular anatomy.

In some embodiments, the distal end of the catheter may be tapered. For example, the tapered profile or outer diameter range may be between 0.5 mm to 1.5 mm and or at an angle between 5 to 30 degrees. The tapered tip 114 may be heat shrunk. In some embodiments, at the most distal segment of the catheter device 101 shaft beyond the distal coiled segment, the outer and inner lining can be heat shrunk to form a 'reflowed' tip 114 without wire reinforcement, thereby conferring to the most distal end of the catheter device 101 a 'soft', atraumatic tip 114.

In some embodiments, the distal end of the catheter device 101 and its tip 114 will be tapered so as to minimize its leading profile. The tapering of the tip 114 may also reduce discrepancies in size between the tip 114 and coaxially telescoped guiding smaller diameter microcatheters and microguidewires. This may allow for atraumatic navigation of the catheter within the cerebral veins while minimizing the risk of intimal dissection Embodiments with the features described herein including, but not limited to, the tappered tip 114, outer jacket 112, inner liner 113, coiled reinforcements 111, and braided reinforcements 110, may be combined, varied, and/or optimized, depending on the extracranial venous access site and the target intracranial vessel segment of interest, to provide an optimal profile of tensile strength for pushability, torqueability, and kink resistance, as well as enhanced flexibility and trackability through the traversed length of the cerebral venous. It is envisioned that different segments of the transvavascular catheter device 101 can be composed of the same or different polymer and reinforcement material(s) as that used in other segments.

Methods and materials for manufacturing of catheters and catheter components used in the access catheter such as access catheter 101 may include the following steps. First, a thin layer of polymer material (e.g., polytetrafluoroethylene (PTFE) or polyimide (PI)) can be extruded through a die or dip coated through a mandrel to achieve a pre-specified catheter inner profile (i.e., inner lining of the catheter lumen(s)). Second, coil, braid, or laser-cut metal hypotube reinforcement element(s), which are independently assembled/manufactured, can be placed over the polymer liner material. In a third step, a thermoplastic elastomer (TPE), such as polyether block amide, can then be heated and extruded through a die to achieve an optimal catheter outer profile and durometer, and placed over the reinforcement braid/coil/hypotube and inner liner. In a fourth step, at a desired temperature and temperature change, the assembled reinforcement material, inner liner and jacket polymers will interfuse, embedding the reinforcement elements within the polymer layers and together forming a catheter shaft. In a fifth step, the outer jacket may be coated with additional hydrophilic or hydrophobic coating. In a sixth step, balloons can be fabricated by expanding compatible materials (balloon blowing) within a mold for a desired shape and compliance. In a seventh step, the balloon stems can be thermally or laser bonded to the catheter shaft at a desired location on the catheter shaft. In an eight step, the catheter central lumen can be fitted with a segregated lumen or lumens. In a ninth step, a segregated lumen can serve as a balloon inflation lumen. In a tenth step, the segregated lumen of the ninth step can be integrated with a stainless steel wire laser bonded to the catheter tip to provide a steering capability. In an eleventh step, exposed compliant wire mesh structures can be integrated with the wire reinforcement embedded in the catheter shaft or bonded to a pull wire. In a twelfth step, a segregated lumen can house a single mode fiber, multimode fiber, a piezoelectric transducer, or a complementary metal-oxide semiconductor.

Embodiments of the disclosed transvascular guide/access catheter device 101 may include a multi-durometer material and/or variably reinforced braided/coiled/laser-etched construct between outer and inner polymeric linings comprising a tubular lumen(s), extra-axial expandable structural member(s)/element(s), a lateral wall working exit lumen port, and a distal end exit port. The embodied catheter device may be optimally configured for use within intracranial cerebral veins and facilitate access to the subdural space, subarachnoid space, or brain parenchyma via the stepwise co-axial introduction of penetrating members, wires, catheters, or other related instrumentation and lateral wall working exit lumen port deployment. Embodiments may include a catheter shaft reinforced by braided, coiled, or laser-etched constructs with variable weave density, picks per inch, or pitch along specific longitudinal segments residing between outer and inner polymeric layers.

In some embodiments, the transvascular guide/access catheter device 101 may include a tubular shaft, proximal port(s), a central lumen operably connected to a lateral wall working exit lumen port and a distal exit lumen port, and extra-axial offset expandable structural member(s)/element(s). In some embodiments, the access catheter device 101 may have expandable compliant extra-axial member(s) located diametrically opposite to the lateral wall or offset working exit lumen port on the catheter shaft between about 1 to 20 millimeters (mm) from the distal end. The working lumen exit port can be located between about 1 to 20 mm from the distal end of the catheter shaft diametrically opposite to the offset compliant expandable structural member, and be configured to facilitate the selective deployment of coaxially-introduced catheters with or without advanced functionality or unique features, as well as transcatheter deliverable instruments or devices, from its working exit lumen port(s).

In some embodiments—(such as those illustrated in FIGS. 2A-3B) an access catheter, such as one analogous to that illustrated in FIGS. 1A-1C, may include a laterally expandable support carried by the elongate, flexible tubular body which is positioned on an opposite side of the tubular body from the side exit port. Examples of laterally expanding supports include inflatable balloons, laterally deflatable struts, and the like.

FIG. 2A-B illustrates an embodiment of an access catheter device featuring an inflatable elastomeric balloon located diametrically opposite to the lateral wall working exit lumen port in accordance with an embodiment of the present disclosure. In particular, FIG. 2A illustrates an embodiment of an access catheter device featuring an inflatable elastomeric balloon in a first state and FIG. 2B illustrates an embodiment of an access catheter device featuring an inflatable elastomeric balloon of FIG. 2A in a second state.

The access catheter device includes a main central lumen 201 with a lateral wall working exit lumen port 202, and a distal end working exit lumen port 203. The catheter may have a reflowed or heat shrunk tapered tip 204, luminal molding 205. The access catheter may also include a selective passageway 206, segregated balloon inflation lumen 207, a balloon inflation port 208, and a compliant elastomeric balloon 209 that is capable of being deflated and/or inflated. A microcatheter 210 and microguidewire 211 may be contained within the assembly. In some embodiments, the access catheter device may be positioned within the cerebral vein 212.

The complaint elastomeric balloon 209 is illustrated in a deflated state in FIG. 2A and in an inflated state in FIG. 2B. The transvascular access catheter device illustrated in FIGS. 2A and 2B can include thermally-bonded compliant elastomeric balloon(s) 209 or an expandable non-occlusive mesh integrated onto the catheter shaft reinforcement material layer (see FIGS. 3A-3B). These expandable members can be mounted extra-axially opposite to the offset of lateral wall working exit lumen port 202. In some embodiments, these compliant structures can, once expanded, position the lateral wall or exit port 202 to the endoluminal surface, as well as provide support and stability to the transvascular catheter system by buffering the back propagation of forward insertion forces as transcatheter tools, devices, or instruments are advanced through the subdural space, subarachnoid space, or brain parenchyma.

In some embodiments, the transvascular guide/access catheter device may have two lumens: (1) one central lumen 201 with a large inner diameter to wall thickness ratio for co-axial catheter and catheter related tools/instruments (e.g., guidewires, needles, etc.) and 2) a second small diameter segregated lumen, such as a balloon inflation lumen 207. The balloon inflation lumen 207 can operably connect to a balloon inflation syringe via the balloon inflation port 208 attached to the proximal end of the catheter and terminate in a compliant or an ultra-compliant elastomeric balloon 209 thermally bonded to the catheter shaft.

In some embodiments, the transvascular guide/access catheter device can have a single offset balloon member 209 located more distally along the catheter shaft diametrically opposite to a lateral wall or offset working exit lumen port 202. The balloon inflation lumen 207 operably connects a proximal port and distal balloon inflation holes, where the balloon inflation lumen may terminate. The offset balloon 209 can be expanded with media (e.g., saline, contrast, etc.) and position and anchor the offset or lateral wall working lumen exit port 202 within a cerebral vein.

In one embodiment, offset compliant or ultra-compliant balloon(s) 209 are bonded to the endovascular catheter shaft opposite a lateral wall working lumen exit port located distally on the endovascular catheter shaft. Associated with the offset balloon 209 can be a method to apposition the lateral wall working exit lumen port with the endoluminal surface of the cerebral vein when the balloon is inflated, such that the lateral wall working exit lumen port is positioned and/or effaces in a specific orientation against the luminal surface of vein prior to creating a venous access site. In some embodiments, the endovascular access or guide catheter can have an outer diameter ranging between 3.9-6.6 French (1.3-2.2 mm). The choice of compliant structure may be an elastomeric balloon material (e.g., polyurethane, silicon, chlonoprene etc.) or a compressible-expandable structural mesh element/member. In its expanded state, the compliant structure(s) function(s) to negate: 1) the radial forces exerted on the endoluminal aspect of the vein, and 2) the backpropagation of forward insertion forces during transvascular penetration and/or catheter advancement through intracranial spaces, tissues, or media. One function of an expandable balloon structure/member featured on or introduced via the proposed access/guide endovascular catheter is to tamponade the venous access site post-procedurally to provide hemostasis.

FIG. 3A-B illustrates an embodiment of an access/guide catheter device featuring a compressible-expandable offset non-occlusive structural element/member located diametrically opposite to the lateral wall working exit lumen port in accordance with an embodiment of the present disclosure. In particular, FIG. 3A illustrates an embodiment of an access/guide catheter device featuring a compressible-expandable offset non-occlusive structural element/member in a first dormant state, and FIG. 3B illustrates an embodiment of an access/guide catheter device featuring the compressible-expandable offset non-occlusive structural element/member of FIG. 3A in a second, expanded and deployed state.

As illustrated in FIGS. 3A and 3B, the access or guide catheter (analogous to those illustrated in FIGS. 1A-2B) may include a main central lumen 301, lateral wall working exit lumen port 302, distal end working exit lumen port 303, a reflowed, or heat shrunk atraumatic tip 304, luminal molding 305, and a selective passageway 306. A mesh sheath 307 may be deployed and then removed from a target area. A complaint wire mesh and non-occlusive balloon may be compressed and/or expanded 308. The access or guide catheter may be positioned within a cerebral vein 309.

In some embodiments, the transvascular guide/access catheter device can have two lumens and a single offset expandable wire mesh structure 307. The offset expandable wire mesh structure 307 can be sheathed and/or compressed via tension applied by a pull-wire, when maintaining a low-profile is desired. Unsheathing or removing tension from the pull-wire allows the compliant wire mesh structure 307 to achieve an expanded state (shown in FIG. 3B). The lateral wall working lumen exit port 302 may be located on the catheter shaft between about 1 to 20 mm from its distal end, and be configured to selectively deploy a coaxially-introduced catheter with or without advanced functionality or unique features from its working exit lumen port(s), as well as transcatheter deliverable instruments or devices.

In some embodiments, the offset complaint, expandable wires or wire mesh 307, which may or may not be polymer coated (e.g., polytetrafluoroethylene, etc.), is bonded onto and/or woven into the endovascular catheter shaft opposite an oblong-shaped lateral wall working exit lumen port located distally on the endovascular catheter shaft. Associated with the offset compliant wire mesh 307 may be a method for juxtaposing the lateral wall working exit lumen port with the endoluminal surface of the cerebral vein when the compliant wire mesh 307 is in its expanded state, such that the lateral wall working exit lumen port 302 effaces the endothelium of the vein prior to creating a venous access site. In some embodiments, an endovascular catheter that can have an outer diameter ranging between 3.9-6.6 French (1.3-2.2 mm) may be used. The choice of compliant wire structure may be nitinol, which may be polymer coated (e.g., with polytetrafluoroethylene, etc.) to minimize endothelial disruption or damage, and it functions to negate excessive radial force exertion on the wall of the housing vein and/or the backpropagation of forward insertion forces exerted during co-axial catheter advancement through intracranial spaces or tissues.

Figure 4B:
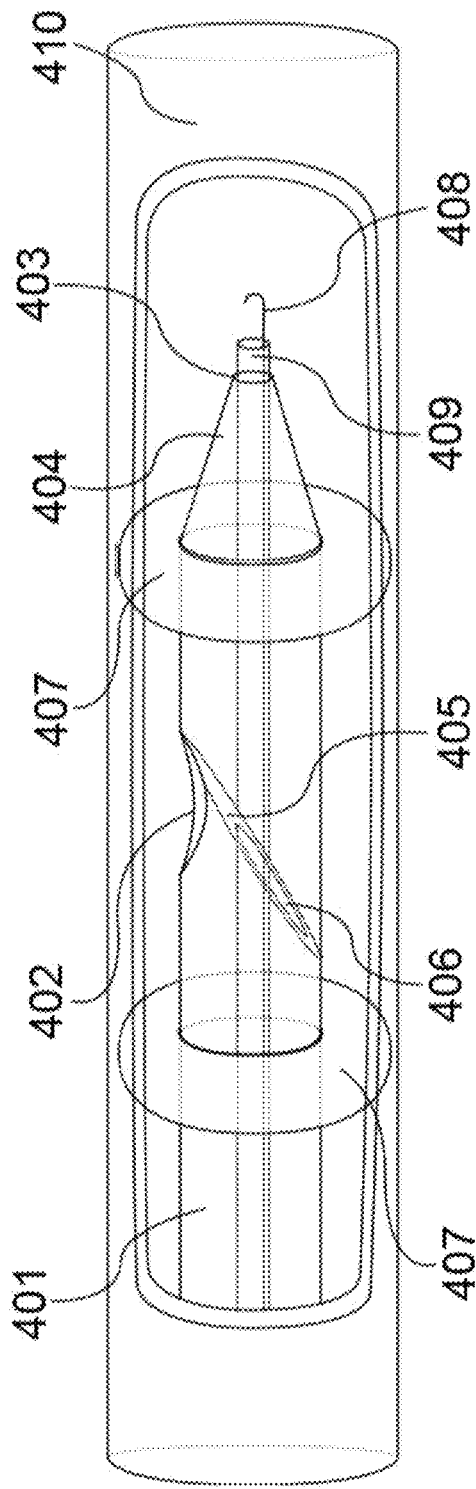
FIG. 4B illustrates an embodiment of an access catheter device featuring inflatable elastomeric double-balloons of FIG. 4A in a second state in accordance with some embodiments of the present disclosure.

FIG. 4A-B illustrates an embodiment of an access catheter device featuring inflatable elastomeric double-balloons in-series flanking the lateral wall working exit lumen port 402 in accordance with an embodiment of the present disclosure. In particular, FIG. 4A illustrates an embodiment of an access catheter device featuring inflatable elastomeric double-balloons in a first dormant, non-deployed state and FIG. 4B illustrates an embodiment of an access catheter device featuring inflatable elastomeric double-balloons of FIG. 4A in a second, deployed, inflated state.

As depicted, the access catheter may include a first occlusion balloon 407A and a second occlusion balloon 407B, where the first occlusion balloon 407A is positioned on the tubular body on a proximal side of the side exit port and the second occlusion balloon 407B is positioned on the tubular body on a distal side of the side exit port. The access catheter may include a main central lumen 401, lateral wall working exit lumen port or side exit port 402, a distal end working exit lumen port 403, a reflowed or heat shrunk tapered tip 404, luminal molding 405, a selective deflector 406, serial compliant elastomeric balloons 407A and 407B, and a microcatheter 409, microguidewire 409. The access catheter may be positioned within a cerebral vein 410.

In some embodiments, the transvascular guide/access catheter can have a first balloon 407A and a second balloon 407B operably connected through the same inflation lumen in a dual lumen catheter design or through distinct inflation holes in single lumen catheter design. In some embodiments, the lateral wall working lumen exit port 402 may be located between about 1 to 20 mm from the distal end of the catheter shaft between the first balloon 407A and the second balloon 407B, wherein the first balloon 407A and the second balloon 407B may together be expanded, and a lateral wall working lumen exit port 402 located proximal to a distal balloon and/or distal to a proximal balloon and be configured to selectively deploy a coaxially-introduced catheter with or without advanced functionality or unique features from its working exit lumen port(s), as well as transcatheter deliverable instruments or devices.

In some embodiments, the thermally bonded balloon(s) includes at least one of polyurethane, chlonoprene, and silicone elastomeric materials. The two balloons 407A, 407B may be arranged in series flanking a lateral wall working lumen exit port 402 located on the lateral aspect of the endovascular catheter wall. Associated with the double balloon in series may be a method for occluding physiologic drainage and retrograde, negative-pressure venous blood flow from entering the venous access site and/or subdural/ aubarachnoid space. In some embodiments, an endovascular guide/access catheter with an outer diameter ranging between 3.9-6.6 French (1.3-2.2 mm) may be used. The choice of compliant structure may be an elastomeric balloon material (e.g., polyurethane, silicon, chloroprene etc.) and it functions to negate prominent radial force exerted on the wall of the housing vein and/or the backpropagation of forward insertion forces exerted during co-axial catheter advancement through intracranial spaces or tissues. Another function of the balloon feature is to tamponade the venous access site after repositioning to provide post procedural hemostasis. The described design may be intended to temporarily occlude the vein, anchor the catheter, and isolate the working exit lumen port from venous blood flow.

FIG. 5A-B illustrates an embodiment of an access catheter device featuring two serially placed compressible-expandable non-occlusive wire mesh support structures 508 flanking the lateral wall working exit lumen port in accordance with an embodiment of the present disclosure. In particular in FIG. 5A, the non-occlusive wire mesh support structures 508 are compressed, and in FIG. 5B, the non-occlusive wire mesh support structures 508 are deployed or inflated.

As illustrated, in some embodiments, the access catheter device may include a main central lumen 501 with a lateral wall working exit lumen port 502 (also known as a side exit port 502), a distal end working exit lumen port 503, an atraumatic tip 504, luminal molding 505 with a selective deflector 506, a mesh sheath 507, and compliant wire mesh non-occlusive balloons 508. The access catheter device may allow for a microcatheter 509 to pass thru using a microguidewire 510. The access catheter device may be introduced into a cerebral vein 511.

In some embodiments, the wire mesh structure 508 includes cross-linked thin nitinol wire, which may be polymer coated with polytetrafluoroethylene and the like. The expandable wire mesh structure can be sheathed with an outer tubular catheter and/or compressed via tension applied with a pull-wire when maintaining a low-profile is desired, such as for endovascular navigation. Unsheathing or removing tension from the pull-wire allows the compliant wire mesh structure to achieve an expanded state.

A compliant wire mesh structure 508 may be expanded in lieu of a balloon structure to provide an anchor for stability and/or buttress the backpropagation of forward insertion forces exerted on the endovascular catheter housing subsequently introduced and co-axially advanced steerable catheters or transcatheter instrumentation.

Illustrated in FIGS. 5A and 5B, two expandable wired structures or wire mesh elements/structures 508 may be arranged in series flanking a lateral wall working lumen exit port 502 located on the lateral aspect of the endovascular catheter wall. In some embodiments, an endovascular guide/ access catheter with an outer diameter ranging between 3.9-6.6 French (1.3-2.2 mm) may be used. The choice of compliant materials for this expandable element/structure 508 may be a plurality of thin strand nitinol, which in turn may be coated with lubricous polymeric materials (e.g., polytetrafluoroethylene, etc.) so as to minimize endothelial disruption or damage.

The expandable wire structures or mesh elements/structures 508 functions to anchor the guide/access catheter in place and negate the prominent radial force exerted on the wall of the housing vein and/or the backpropagation of forward insertion forces exerted during co-axial catheter advancement through intracranial spaces or tissues.

Figure 6A:
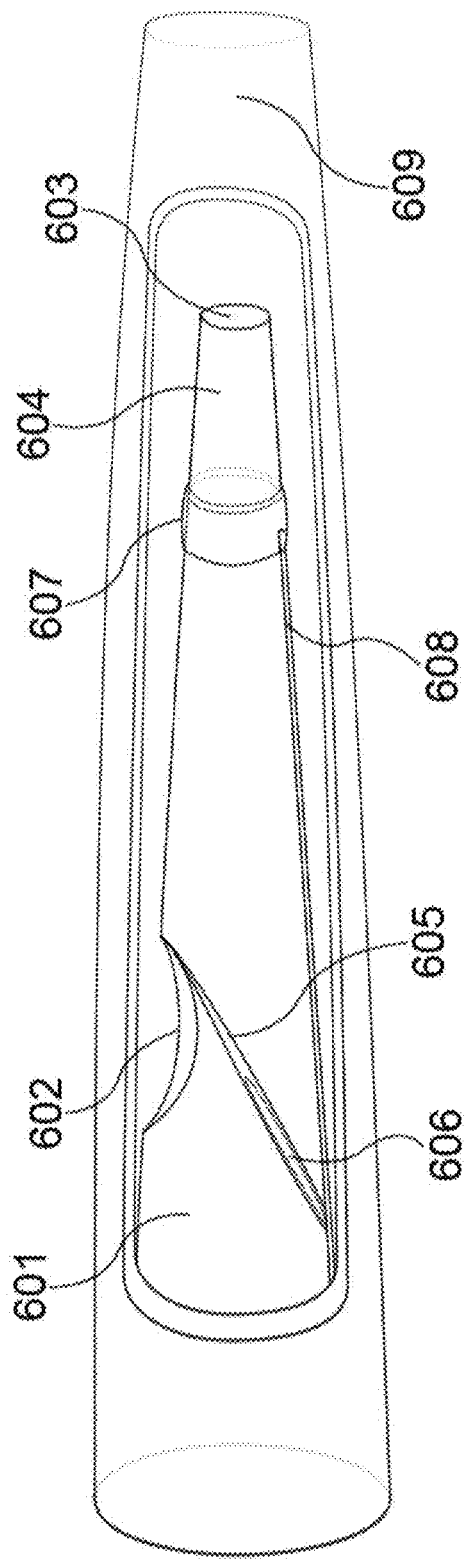
FIG. 6A illustrates an embodiment of a hybrid-sized catheter device featuring an inflatable elastomeric balloon in a first state in accordance with some embodiments of the present disclosure.
Figure 6B:
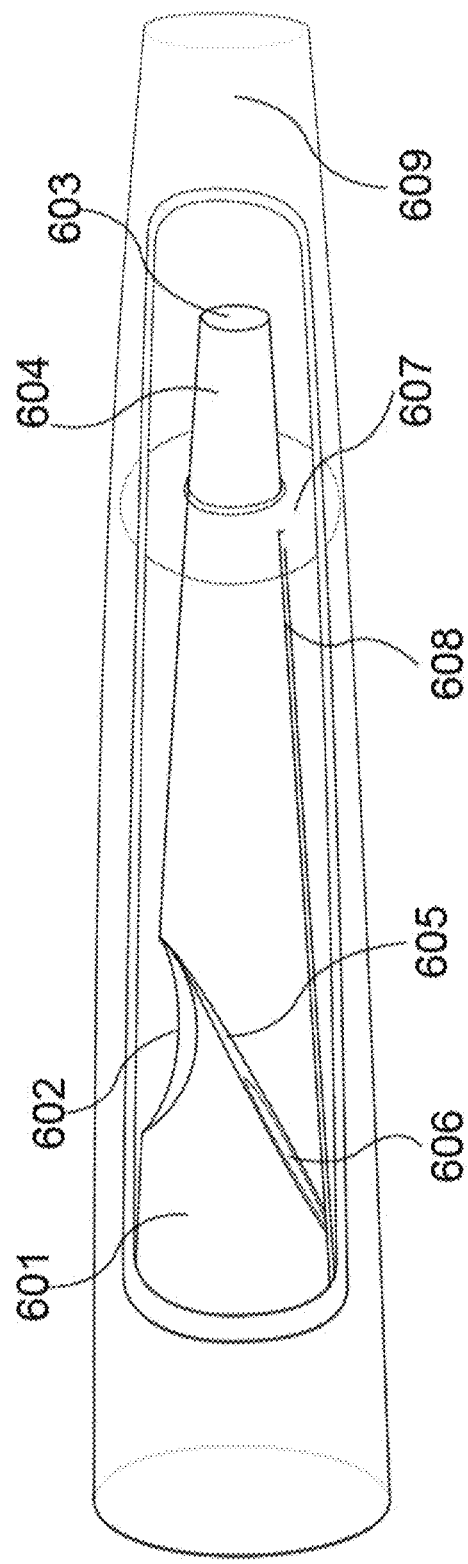
FIG. 6B illustrates an embodiment of a hybrid-sized catheter device featuring an inflatable elastomeric balloon of FIG. 6A in a second state in accordance with some embodiments of the present disclosure.

FIGS. 6A-B illustrate an embodiment of a hybrid-sized catheter device featuring an inflatable elastomeric balloon 607 distal to the lateral wall working exit lumen port in accordance with an embodiment of the present disclosure. The hybrid-sized catheter illustrated in FIGS. 6A-B may include a main central lumen 601, a lateral wall working exit lumen port 602, a distal end working exit lumen port 603, a tapered tip 604, a selective deflector 606 with luminal molding 605. The hybrid-sized catheter device may include compliant elastomeric balloons 607 illustrated in a deflated state in FIG. 6A and an inflated state in FIG. 6B. The balloon 607 may be configured to be inflated/deflated by way of a segregated balloon inflation lumen. The hybrid-sized catheter device may be positioned within a cerebral vein 609.

As illustrated, the hybrid-sized distal balloon catheter may have a more proximal offset or lateral wall working lumen exit port 602 emanating from a wider diameter segment proximal to the proximal end of the catheter shaft. In some embodiments, the described system may be intended for use in the deep cerebral veins where rapid tapering of vein diameters in rostral proximal draining segments have been reported on prior venography studies.

An associated microcatheter scaled end {with an outer diameter=between about 1.2-3.2 French or 0.4-0.8 mm} may be intended to access the narrow, rostral segments of deep cerebral veins atraumatically. The distal compliant/ ultra-compliant structural component such as balloon 607 located on the distal microcatheter end may be inflated to temporarily occlude physiologic venous drainage and/or anchor the catheter device via similar mechanisms of inflation used in conventional balloon catheters described herein.

The wide diameter, more proximal portion of the catheter shaft may feature the offset or lateral wall working lumen exit port 602, which may be contiguous with the main lumen of the access catheter allowing for 1.925 mm or less outer diameter range coaxial catheters and 18-34-gauge sheathed flexible needles.

The disclosed design may be optimized for delivery of biopotential sensing/stimulating/modulating devices into the subcortical nuclei or for biopsy and ablation of deep-seated lesions. The described design may be intended to temporally occlude the vein and isolate the working exit lumen port 602 from physiologic venous blood flow, anchor the endovascular catheter in place to stably guide the insertion of penetrating instruments into brain tissue or media, and provide post-procedural hemostasis by direct tamponade with inflation.

FIGS. 7A-B illustrate an embodiment of a hybrid-sized catheter device featuring a compressible-expandable non-occlusive wire mesh support distal to the lateral wall working exit lumen port in accordance with an embodiment of the present disclosure. The hybrid-sized catheter device includes a main central lumen 701 with a lateral wall working exit lumen port 702, distal end working exit lumen port 703, an atraumatic tip 704, and a selective deflector 706 formed of luminal molding 705. The hybrid-sized catheter device may include a compliant and compressible expandable non-occlusive wire mesh support 708 which may be compressed (as illustrated in FIG. 7A) and/or expanded (as illustrated in FIG. 7B) by way of a mesh pullwire 707. The hybrid-sized catheter device may be positioned within a cerebral vein 709.

The wire mesh support 708 may be formed of an expandable cross-linked nitinol and be located proximal the working lumen exit port of the hybrid catheter 703 emanating from the catheter shaft. The distal expandable mesh component 708 located on the distal microcatheter end may be intended to anchor the catheter in place during transvascular puncture or insertion into brain tissue or media. The choice of compliant materials for this expandable element/structure 708 may be a plurality of thin strand nitinol, which in turn may be coated with lubricous polymeric materials (e.g., polytetrafluoroethylene, etc.) so as to minimize endothelial disruption or damage. The wide diameter, more proximal portion of the catheter shaft may feature the offset or lateral wall working exit lumen port 702, which can be contiguous with the main lumen of the access catheter allowing for 1.925 mm or less outer diameter range coaxial catheters, penetrating members, or 18 gauge or smaller flexible needles. The disclosed design may be optimized for delivery of biopotential sensing/stimulating/modulating devices into the subcortical nuclei or for biopsy and ablation of deep-seated lesions. In some embodiments, the described system may be advantageously used in for longer duration procedures where prolonged venous stasis or occlusion may result in thrombus formation and/or venous hypertension, respectively.

FIG. 8A-E illustrate a sequence of process steps enabled by an embodiment of the access catheter device residing in a cerebral vein of interest to mediate transvascular access to tissue/media in the intracranial vault in accordance with an embodiment of the present disclosure.

The transvascular access catheter device embodiments described herein are introduced from an extracranial vein and advanced intravenously/endovascularly for use in the intracranial cerebral venous system of a human or an animal to mediate access to extravascular spaces within the intracranial vault. As depicted in FIGS. 8-10, the transvascular access catheter device in some embodiments can be introduced at a convenient entry point from an extracranial vein (e.g., subclavian vein, internal jugular vein, or femoral vein, etc.) through a guiding member (i.e., shuttle sheath).

The transvascular access catheter device can then be advanced to a desired intracranial location within a vein over telescoped co-axial guiding members emanating from its distal end exit port, which feature 'soft' tip(s) and distal end radiopaque markers or fillers to aid in visualization. Once situated in a desired location within an intracranial vein, these telescoped guiding members may be removed. A second marker located adjacent to the lateral wall opening or offset port may direct the user to rotationally adjust the transvascular access catheter device, such that a transcatheter penetrating device may be deployed from the lateral wall opening or offset port over a selective deflecting member to puncture through the vein from its endoluminal side and advanced transmurally in a trajectory that minimizes the potential for parenchymal damage. The created venous puncture site creates an entry point for guidewires, catheters, transcatheter instruments, and implants to be introduced into the subdural or subarachnoid space or directly into the brain parenchyma.

Figure 8A:
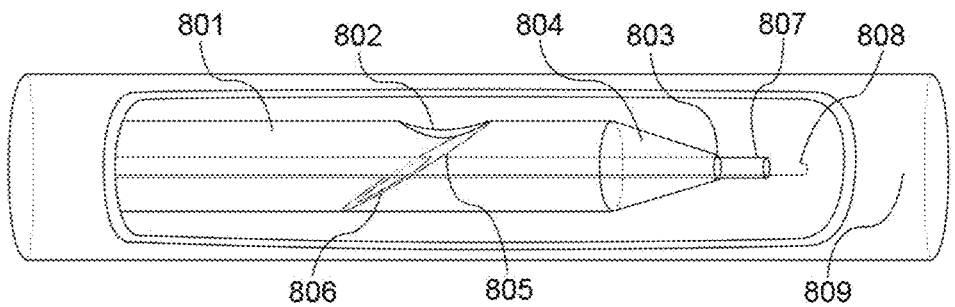
FIG. 8A illustrates a first step in a sequence of process steps enabled by an embodiment of the access catheter device residing in a cerebral vein of interest to mediate transvascular access to tissue/media in the intracranial vault in accordance with some embodiments of the present disclosure.

A method for accessing a desired target intracranial location using a transvascular access catheter is depicted in FIGS. 8A-8E. In particular FIG. 8A illustrates cerebral venous access using a microguidewire and microcatheter coaxially advanced through the selective passageway and deployed from the distal end working exit lumen port of the guide/access catheter. In a first step an endovascular access/guide catheter 801 may be positioned within a cerebral vein 809 using a 0.014 or 0.018 inch microguidewire 808, co-axially introduced through a microcatheter 807, which may feature built-in pull-wires for steerable capabilities, together in a telescoped configuration. The endovascular access/guide catheter 801 may include a side exit port or a lateral working lumen exit port 802 and a distal working lumen exit port 803. The endovascular access/guide catheter 801 may also include a selective deflector 805 with luminal molding 806. Inflation or expansion of a compliant structure (bonded balloon(s) or wire mesh structural member(s)) may be used to maintain the position of the lateral working exit lumen port near/against the endoluminal surface of the vein at an entry point of interest. Additionally, inflation or expansion of the same compliant structure(s) (e.g., balloon(s) or wire mesh structural member(s)) may also be used to provide a buffer against the back propagation of forward insertion forces.

Figure 8B:
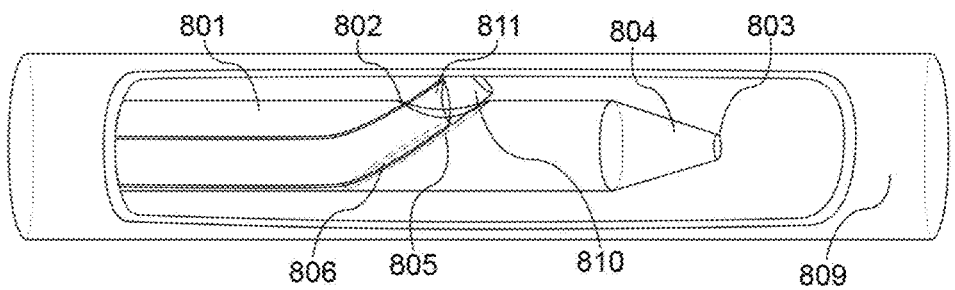
FIG. 8B illustrates a second step in a sequence of process steps enabled by an embodiment of the access catheter device residing in a cerebral vein of interest to mediate transvascular access to tissue/media in the intracranial vault in accordance with some embodiments of the present disclosure.

FIG. 8B illustrates removal of the microcatheter and microguidewire from guide/access catheter shaft lumen.

Figure 8C:
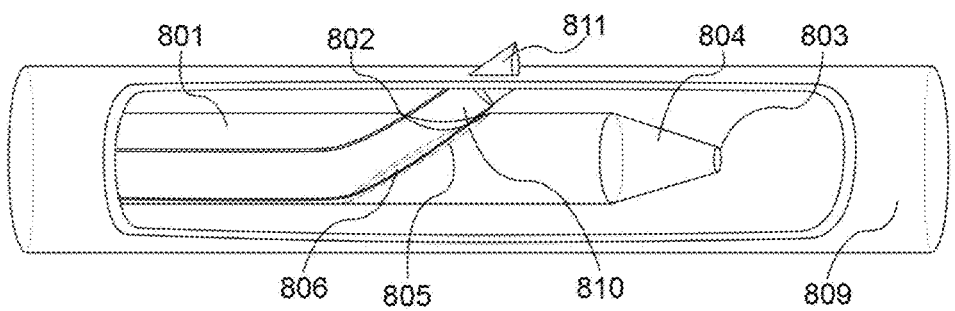
FIG. 8C illustrates a third step in a sequence of process steps enabled by an embodiment of the access catheter device residing in a cerebral vein of interest to mediate transvascular access to tissue/media in the intracranial vault in accordance with some embodiments of the present disclosure.

FIG. 8C illustrates co-axial introduction and deployment of a catheter or related instrumentation 811 through the lateral wall working exit lumen port 802. A retractable needle sheath 810 may facilitate needle delivery without damaging the inner liner as it is co-axially delivered within the main catheter lumen through tortuous venous anatomy.

Figure 8D:
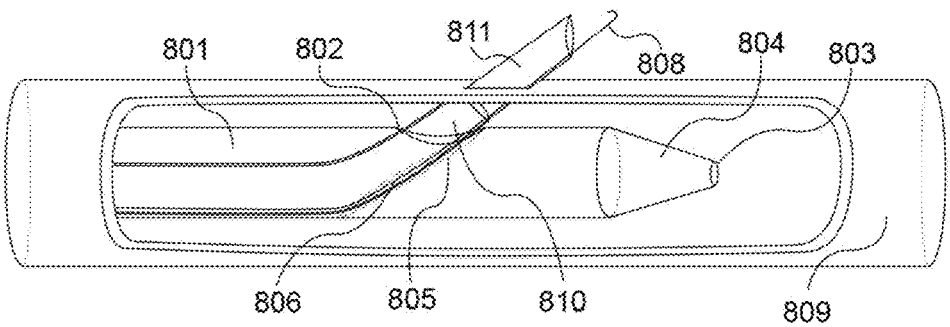
FIG. 8D illustrates a fourth step in a sequence of process steps enabled by an embodiment of the access catheter device residing in a cerebral vein of interest to mediate transvascular access to tissue/media in the intracranial vault in accordance with some embodiments of the present disclosure.

FIG. 8D illustrates transvenous and/or transdural puncture with a penetrating member across the vessel wall and into the brain parenchyma, subdural or subarachnoid space. In some embodiments, the vessel, and if applicable, the encasing dura, may be punctured with a penetrating catheter or needle from the lateral wall working exit lumen port into a perivascular space.

Figure 8E:
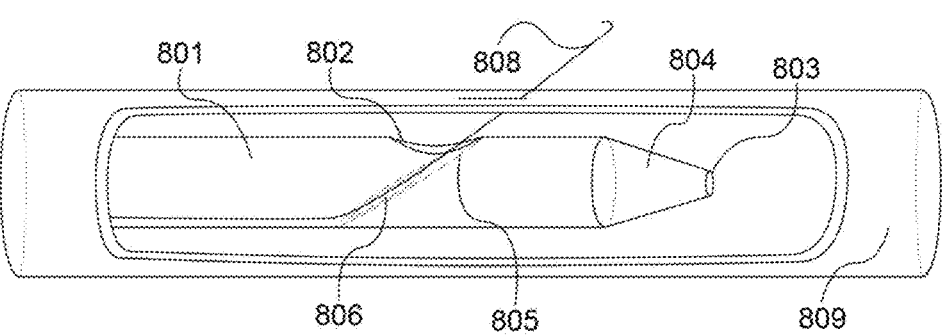
FIG. 8E illustrates a fifth step in a sequence of process steps enabled by an embodiment of the access catheter device residing in a cerebral vein of interest to mediate transvascular access to tissue/media in the intracranial vault in accordance with some embodiments of the present disclosure.

FIG. 8E illustrates transvascular advancement and placement of a guidewire through the penetrating member into the brain parenchyma, subdural and/or subarachnoid space to guide subsequently introduced co-axial catheters or instrumentation. The guidewire may then be advanced through the penetrating catheter or needle into a perivascular space. The guidewire may then be retracted from the penetrating catheter or needle with the guidewire placed across the venous puncture site. A dilating catheter may be co-axially introduced via over the wire techniques through a flexible, 'soft' tip catheter deployed from the lateral wall working lumen exit port across the venous puncture site and into the subdural space. The sub dural space may be navigated with a flexible, 'soft' tip catheter equipped with remote steerability control.

The methods described herein may be used for the transcatheter deployment or delivery of a flexible brain biopsy-needle, a single or a multi-mode optical fiber for in situ imaging or a laser interstitial thermal therapy, respectively, a self-expandable electrode array, or an implantable nanofluidic apparatus. These transcatheter devices or implants and the methods described herein may be used to diagnose, treat, or investigate intracranial tissue or media in an anatomical boundary of interest located a distance (i.e., centimeters) from the transvascular puncture site. Catheters or transcatheter instruments may facilitate implantation, anchoring, or retrieval of a device. During or after the transvascular procedure, a balloon member located near, at, or beyond the distal end of the catheter may either be deflated to allow for rotational or axial repositioning of the endovascular catheter within the punctured vein. An elastomeric compliant or ultra-compliant balloon member may then be inflated over the transvascular puncture site to seal or tamponade the vascular wall defect. In some instances, a bioreabsorbable hemostatic material may be deployed over the transvascular access site to achieve hemostasis.

As illustrated, the access catheter 801 may be positioned within the vein 808 using a guide catheter co-axially introduced over a guidewire and advanced through a selective passageway (<0.87 mm) and deployed from the distal end working exit lumen port 803 of the guide/access catheter 801. The microcatheter and guidewire may be retracted from the central lumen of the guide/access catheter 801. In some embodiments, a flexible access needle may be co-axially introduced into the central lumen of the guide/access catheter. In a next step, a complaint structure (or structures) is (are) expanded, positioning the lateral wall working lumen exit port against the intended venous access site. In a next step, a flexible needle coated with polymeric material (e.g., polytetrafluoroethylene, etc.) and/or sheathed in a retractable guard or catheter may be selectively deployed out of the lateral wall working exit lumen port 802. In a next step, the flexible needle penetrates transmurally across the vessel wall being reinforced with a stylet for tensile strength. After puncturing across the vein, the stylet is withdrawn and a guidewire is advanced co-axially through the unreinforced flexible needle, such that it abuts the encasing dural layer. The flexible needle is withdrawn leaving the guidewire in place across the venous puncture site and abutting the encasing dura as a placeholder.

FIG. 9A-D illustrate a sequence of process steps enabled by embodiments of the access catheter to provide post-procedural hemostasis at the transvascular puncture site in accordance with an embodiment of the present disclosure. As illustrated, the guide/access catheter 901 may include a lateral wall working exit lumen port 902, a selective deflector 905 with luminal molding 906, a tapered tip 904, and a distal end working exit lumen port 903. As illustrated in FIGS. 9A-D, the access catheter 901 may be positioned within a cerebral vein 908.

Figure 9A:
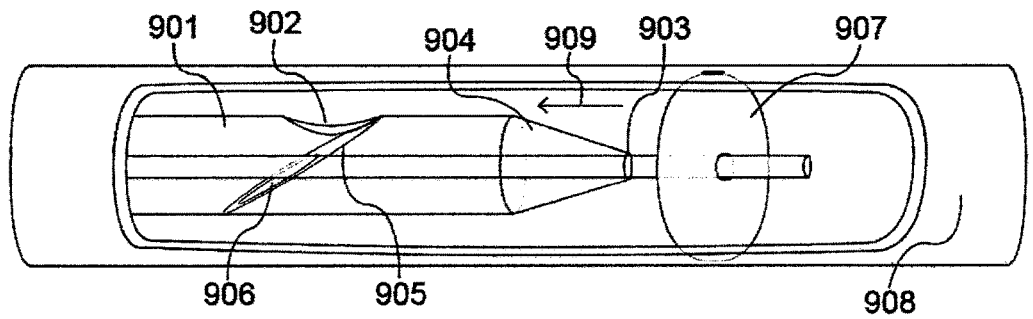
FIG. 9A illustrates a first step in a sequence of process steps enabled by embodiments of the access catheter to provide post-procedural hemostasis at the transvascular puncture site in accordance with some embodiments of the present disclosure.
Figure 10:
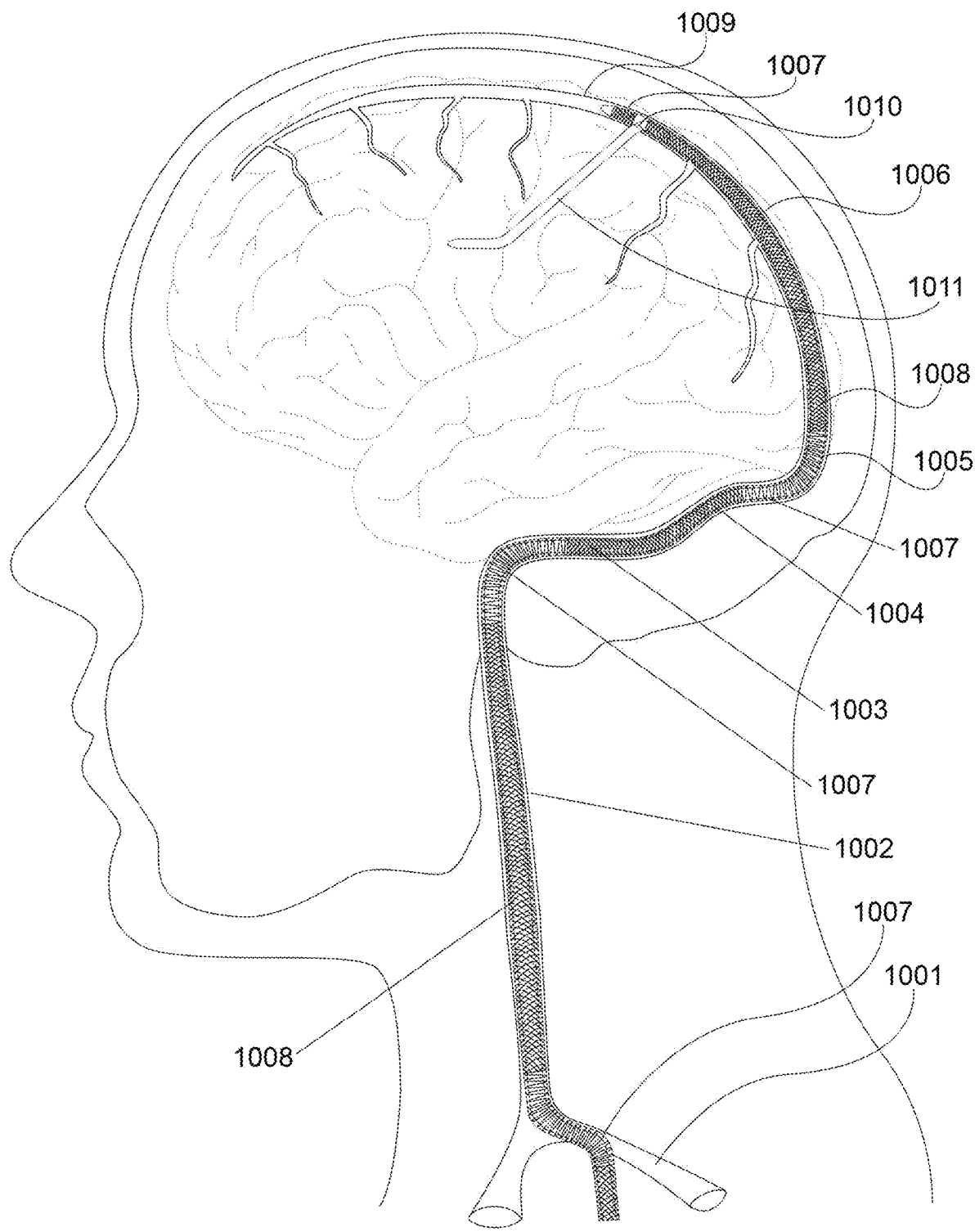
FIG. 10 illustrates an embodiment of the catheter shaft featuring discreet segments of alternating reinforcement members along its longitudinal extent in accordance with some embodiments of the present disclosure.

In particular, FIG. 9A illustrates pulling back 909 the guide/access catheter 901 such that a balloon microcatheter 907 may be deployed from the distal end working exit lumen port 903 to tamponade the venous puncture site for hemostasis.

Figure 9B:
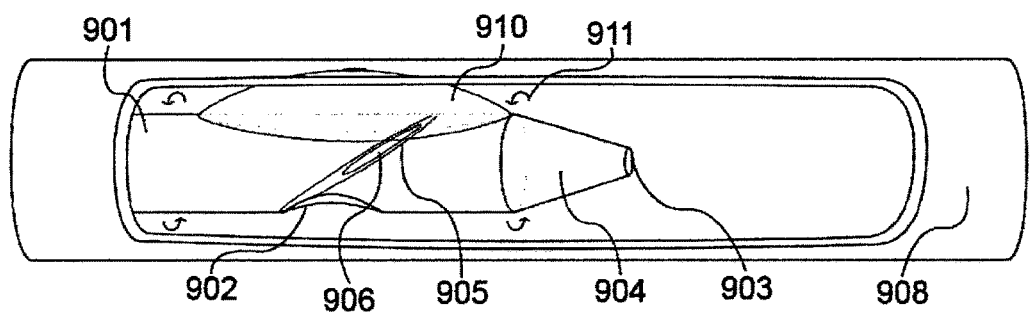
FIG. 9B illustrates a second step in a sequence of process steps enabled by embodiments of the access catheter to provide post-procedural hemostasis at the transvascular puncture site in accordance with some embodiments of the present disclosure.

FIG. 9B illustrates rotating the guide/access catheter such that the offset balloon 910 may be positioned opposite to the lateral wall working exit lumen port to tamponade the venous puncture site for hemostasis.

Figure 9C:
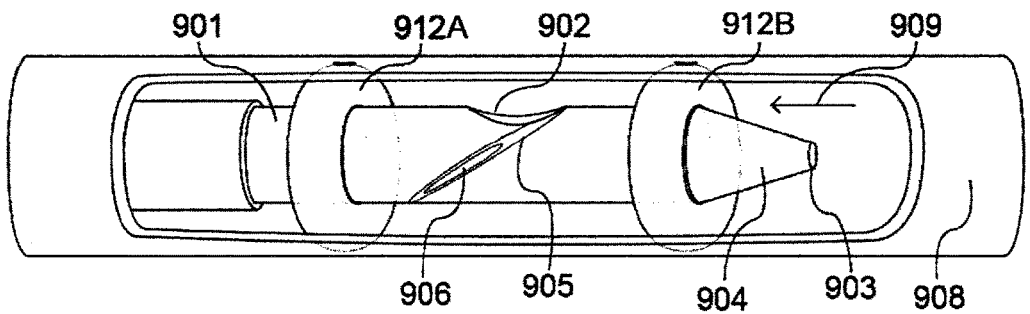
FIG. 9C illustrates a third step in a sequence of process steps enabled by embodiments of the access catheter to provide post-procedural hemostasis at the transvascular puncture site in accordance with some embodiments of the present disclosure.

FIG. 9C illustrates axially repositioning the guide/access catheter such that one or more balloons positioned on the catheter shaft may be inflated to tamponade the venous puncture site for hemostasis. The catheter may include either an offset expandable structure 901, a distal expandable structure 913, a proximal expandable structure 912A spaced apart from a distal expandable structure 912B, and a lateral wall working lumen exit port 902 that may be positioned opposite to, proximal to, or between two expandable structure(s) 912A, 912A.

Figure 9D:
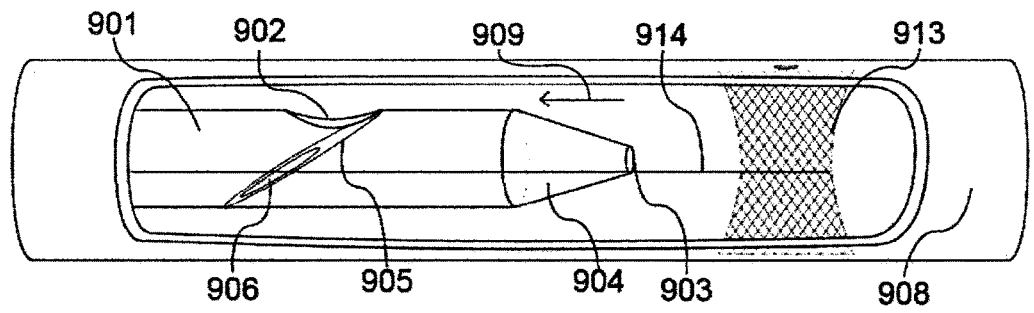
FIG. 9D illustrate a fourth step in a sequence of process steps enabled by embodiments of the access catheter to provide post-procedural hemostasis at the transvascular puncture site in accordance with some embodiments of the present disclosure.

FIG. 9D illustrates the deployment of a bioresorbable hemostatic material or mesh 913 from the guide/access catheter working exit lumen port(s) over the venous puncture site for hemostasis.

FIGS. 9A-9D illustrate a method for providing percutaneous transvascular access to a brain or subdural/subarachnoid space. In a first step, a catheter 901 is positioned within a cerebral vessel 908 adjacent to the brain area of interest using a guidewire and/or microcatheter with or without steerable functionality. In some embodiments, the catheter 901 may include a lumen, a single expandable element 907 or 910, or a first expandable structural element/member 912A and a second expandable structural element/member 912B spaced apart from the first expandable structural element(s)/member(s) 912A, and a lateral wall working lumen exit port 902 opposite to, between, or proximal to expandable structural element(s)/member(s).

Further, in some embodiments the first expandable structural element or member, balloon 912A and the second balloon 912B may be connected via a lumen, and the working lumen exit port 902 may be located between the first balloon 912A and the second balloon 912B. In some embodiments the first expandable structural member(s)/element(s) 912A and the second expandable structural element/member 912B may be sheathed or share a common pullwire for compression into a low profile state, and lateral wall working lumen exit port 902 may be located between the first balloon 912A and the second balloon 912B. Once the catheter 901 is positioned, in a second step, the microcatheter and guidewire, if utilized, may be retracted 909. In a next step, the compliant structure(s)/element(s) on the catheter shaft 907, 910, 912A, 912B, 913 may be expanded/inflated.

In a next step a flexible hollow needle or puncturing cannula sheathed in a protective tubular lumen may be deployed from the lateral wall working exit lumen port 902. The flexible needle may be reinforced (not depicted) with a stylet for tensile strength. A wire may be introduced through the access needle once the vascular wall is punctured and traversed and the stylet removed. The wire or a catheter may be left in place across the vascular wall as a placeholder to guide transvascular catheter placement through the previously established venous puncture site. A catheter with advanced functionality may be advanced over the wire through the guide/access catheter and then deployed into the brain area of interest (parenchyma, subdural, or subarachnoid space) from the lateral wall working exit lumen port.

More particularly, a needle or a penetrating member may be advanced into a peripheral vascular access site from a suitable vessel (e.g., subclavian vein, internal jugular vein, brachial vein, femoral vein and the like). In a next step, a wire may be advanced through the needle or penetrating member. In a following step, a support sheath may be advanced over the wire. In a next step, the guide/access catheter is advanced through a support sheath. In a next step, a microcatheter may be navigated distal to the intended transvascular puncture site from within the endolumen of the vein over a microguidewire. The microcatheter can have steerable functionality. Then the guide/access catheter may be advanced over the telescoped microguidewire-microcatheter system to a suitable cerebral vein within the intracranial vault. Then the lateral wall working exit lumen port of the guide/access catheter may be rotationally positioned over the intended venous puncture site from within the endolumen of the vein. Compliant structural member(s)/element(s) of the guide/access catheter are inflated/expanded to optimally position the lateral wall working exit lumen port and anchor the entire catheter system in place. The distal access microcatheter and microguidewire may then be removed from the guide/access catheter. A flexible or steerable needle/wire encased in a second catheter or retractable protective sheath may then be introduced through the lateral wall working exit lumen port of the guide/access catheter. In some embodiments, the flexible biopsy needle may include an 18-34 Gauge needle.

The flexible and/or steerable needle may then, in an eleventh step, be unsheathed from its protective housing to mediate transvascular puncture from the endoluminal site and into the perivenular, subdural or subarachnoid space. After the transvascular puncture, a guidewire may, in twelfth step, be introduced through the flexible needle and maintained transvascularly, across the vessel wall, as a venous puncture site placeholder prior to the removal of the flexible/steerable needle. In a thirteenth step, the needle may be withdrawn leaving only the guidewire in place with its proximal end emanating from the lateral wall working exit lumen port and its distal end residing in brain parenchyma, subdural or subarachnoid space.

In a next step, an advanced functionality catheter with steerable capabilities can be introduced over a wire into the subdural or subarachnoid space over the cortical surface. In some embodiments, the advanced functionality catheter can include flexible needles sheathed in a retractable guard, trocars, dilators, electrode embedded catheter, convection enhanced drug delivery catheters, imaging elements, devices, or apparatuses, or ablation elements, devices, or apparatuses and the like. In a next step, the advanced functionality catheter may be used to perform intracranial transvascular direct brain access procedures (e.g., biopsy, electrode placement, stimulator placement, tissue/media thermal energy delivery, direct drug delivery, device placement). In some embodiments, the advanced functionality catheter may be a steerable catheter equipped with electrodes or configured to deliver implantable recording and/or stimulating electrodes or arrays.

In some embodiments, the advanced functionality catheter can be a steerable catheter configured to deploy a flexible biopsy needle equipped with or housing a single mode fiber for in situ imaging with optical coherence tomography. In some embodiments, the advanced functionality catheter can be a microcatheter equipped with or housing either a multimode fiber for thermally ablating tissues, media, and the like within the intracranial vault. Advantageously, the multimode fiber can be configured for both laser interstitial thermal therapy and volumetric photoacoustic imaging. In some embodiments, the catheter may house or be equipped with a Fiber Bragg Grating Sensor to enable force or temperature measurements.

In some embodiments, a steerable catheter can be configured to deploy a monopolar electrode or like device for thermally ablating tissues. In some embodiments, a catheter housing or equipped with an optical coherence tomography configured single mode fiber, a photoacoustic imaging configured mulitmode fiber, piezoelectric ultrasound image transducer, or computer metal-oxide semiconductor camera for real-time in situ imaging. In some embodiments, these imaging modalities may be combined with a thermal ablating component, functionality, or device, such as a multimode fiber, to enable real-time imaging of ablated tissues. In some embodiments, the advanced functionality catheter may be configured with plurality of optical fibers to enable both real time in situ imaging, temperature monitoring, and ablation in alternating or simultaneous fashion. In other embodiments, the advanced functionality catheter may include a micro-catheter configured with a plurality of lumens for convection enhanced direct drug delivery. In some embodiments, the advanced functionality catheter may be a steerable catheter configured to deploy and implant biodegradable drug delivery nanofluidic devices or apparatuses (e.g., fabricated with materials, such as polydimethylsiloxane, silk, magnesium, etc.) with dose-controlled drug eluting capabilities.

In some embodiments, the expandable compliant structure(s) remain expanded and serve to isolate the lateral wall working lumen exit port, preventing cerebral vein/sinus blood flow from entering into the subdural/subarachnoid space. In some embodiments, the lateral wall working exit lumen port is configured to be contiguous with the catheter's main central lumen. In some embodiments, an internal structure, such as a luminal molding, within the tubular lumen of the catheter shaft serves to selectively guide larger co-axial catheters (>0.9 mm) through the lateral wall working exit lumen port. In embodiments, the guide/access catheter may be advanced to a distally located cerebral vein within the intracranial vault and reside a distance from a brain parenchymal, subdural or subarachnoid area of interest.

In some embodiments, an advanced functionality catheter, such as a steerable catheter, may be co-axially introduced through the central lumen over the placeholder guidewire, exit the lateral working exit lumen port, and advance across the vessel wall such that the steerable catheter can enters the subdural or subarachnoid space where it may be navigated atraumatically to a remote site within the intracranial vault.

Further, the advanced functionality catheter may be removed/withdrawn from the embodied guide/access catheter. And the guide/access catheter may be configured to deploy a bioresorbable hemostatic material configured for endothelial repair of the venous puncture site. A catheter-deliverable hemostatic biodegradable material may be introduced or implanted, such that it resides/overlays the transvascular puncture site.

FIG. 10 illustrates an embodiment of the catheter shaft featuring discreet segments of alternating reinforcement members along its longitudinal extent in accordance with an embodiment of the present disclosure. The access catheter is depicted as accessing distal cerebral veins/sinuses from a peripheral site, and transvascularly deploy a steerable catheter from its lateral working exit lumen port, which in turn enables subdural/subarachnoid navigation of the intracranial space. As illustrated in FIG. 10, the guide/access endovascular catheter shaft is variably reinforced with braids along longitudinal segments of the cerebral venous anatomy and reinforced with coils where flexures/bends are present along tortuous segments of the cerebral venous anatomy. Distal to the lateral wall working exit lumen port, a segment of the guide/access catheter shaft may be coil reinforced to aid in the guide/access catheter's trackability and navigability through tortuous cerebral vessels. The most distal segment of the guide/access catheter may be heat shrunk or reflowed for a soft, atraumatic tip. An embodiment of the steerable catheter may feature a steering collar proximal to a lateral wall or distal end working exit lumen port laser-welded to a pull wire residing within a segregated lumen of the guide/access catheter shaft.

Discrete longitudinal segments with alternating and variable reinforcement material to optimize the guide/access catheter's trackability through the tortuous cerebral venous system and the guide/access catheter's kink resistance at major stress points at acute flexures are illustrated. The transvascularly deployed steerable catheter is illustrated navigating the subdural/subarachnoid space and agile deployment of instruments, devices, cyto-active agents/compounds/materials, or implants. Illustrated in FIG. 10 is the peripheral access site 1001 such as a subclavian vein, the internal jugular vein 1002, the sigmoid sinus 1003, transverse sinus 1004, torcula herophili 1005, and superior sagittal sinus 1006. The device may include a variable pitch coiled reinforcement 1007, variable pick per inch braided reinforcement 1008, distal reflowed/heat shrunk tip 1009, a lateral wall working exit lumen port 1010, and a co-axially offset deployed steerable catheter 1011.

Figure 11A:
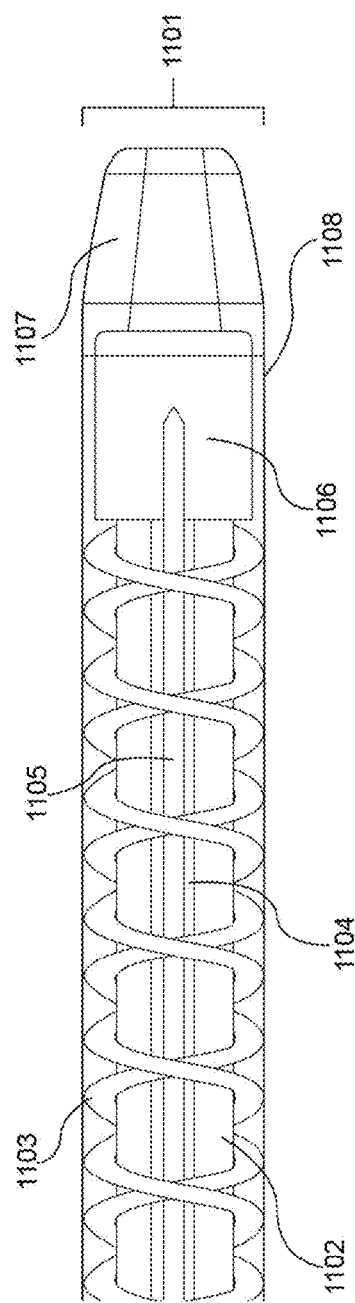
FIG. 11A illustrates an embodiment of the steerable catheter in accordance with some embodiments of the present disclosure.
Figure 11B:
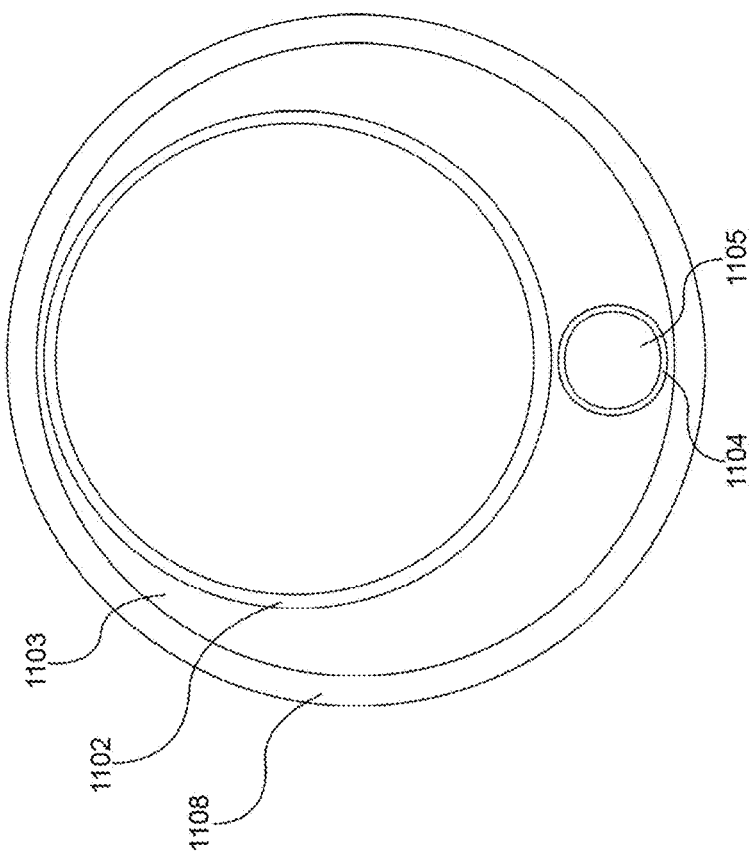
FIG. 11B illustrates a cross-sectional view of the steerable catheter of FIG. 11A in accordance with some embodiments of the present disclosure.

FIG. 11 illustrates an embodiment of the steerable catheter with braided reinforcement and a pull-wire laser welded to a steering collar for navigating spaces within the intracranial vault in accordance with an embodiment of the present disclosure. Illustrated in FIG. 11A is a steerable catheter with braided reinforcement patterns and variable pick per inch 1101, and a cross section thereof in FIG. 11B. The steerable catheter 1101 includes a polymeric liner 1102, braided reinforcement material 1103, a pullwire 1104, steering collar 1105, an atraumatic tip 1106, and an outer polymeric jacket 1107.

Figure 12:
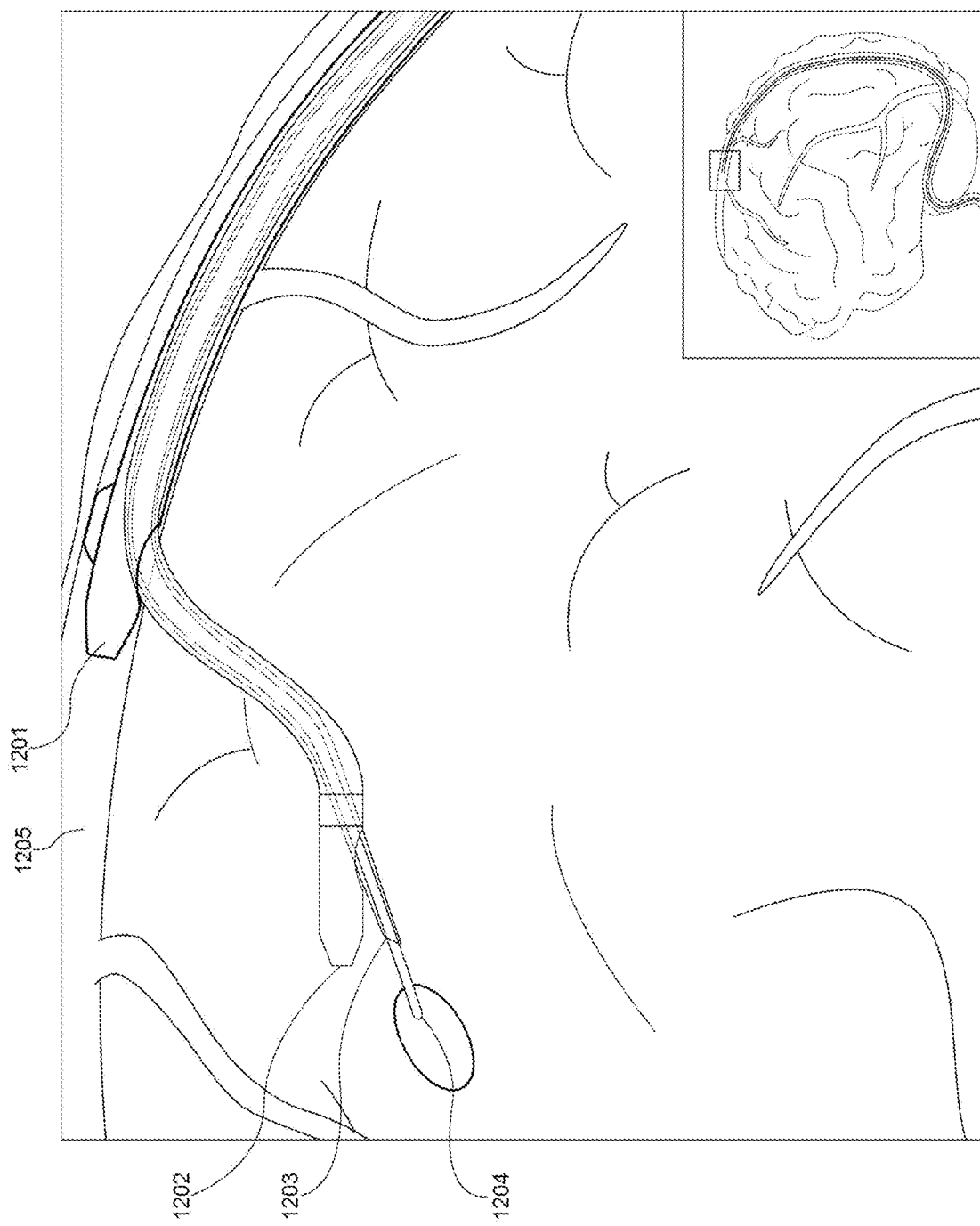
FIG. 12 illustrates a access catheter device mediating extravascular navigation with a transvascularly-introduced steerable catheter in accordance with some embodiments of the present disclosure.

FIG. 12 illustrates a process and an embodiment of the access catheter device mediating extravascular navigation with a transvascularly-introduced steerable catheter featuring a lateral wall working exit lumen port from which a deployed flexible biopsy needle and a through-the-needle deployed microcatheter housing one or more single and/or multimode optical fibers for in situ imaging, sampling, and/or ablating of tissue/media contents in accordance with an embodiment of the present disclosure.

Illustrated in FIG. 12 is an embodiment of an transvascular access/guide Catheter 1201 with an offset balloon built in accordance with the description herein. A steerable catheter is deployed into the subdural space from the lateral wall exit lumen port of the lateral wall exit lumen port of the access/guide catheter 1202. A procedure catheter including a flexible biopsy needle 1203 may be precisely deployed from the steerable catheter's lateral wall working exit lumen port 1202. Further, a fiber optic equipped microcatheter 1204 may be deployed through the needle. The assembly may be used within the cerebral vein or sinus 1205 including, for example, the superior sagittal sinus.

In some embodiments, the procedure catheter may include at least one of a flexible needle, a steerable needle, a retractable needle sheath, a retractable guard, a dilator, a steerable catheter, an imaging device, an ablation device, force sensors, temperature sensors, biopsy device, a compressible-expandable biopotential sensing or stimulation device or implant, a convection-enhanced drug delivery microcatheter, or an injectable drug eluting bioresorbable nanofluidic implant. An ablation device or imaging device may also include a microelectronic mechanical system, optical technology, a flexible laser-cut hypotube, or co-axial actuating mechanical system. In some embodiments, the compressible-expandable biopotential sensing or stimulation device or implant may include a shape memory scaffold embedded with electrodes configured to transmit to a connector for recoding neurons, mapping cortical activity, stimulating neurons, or modulating cortical activity.

Figure 13:
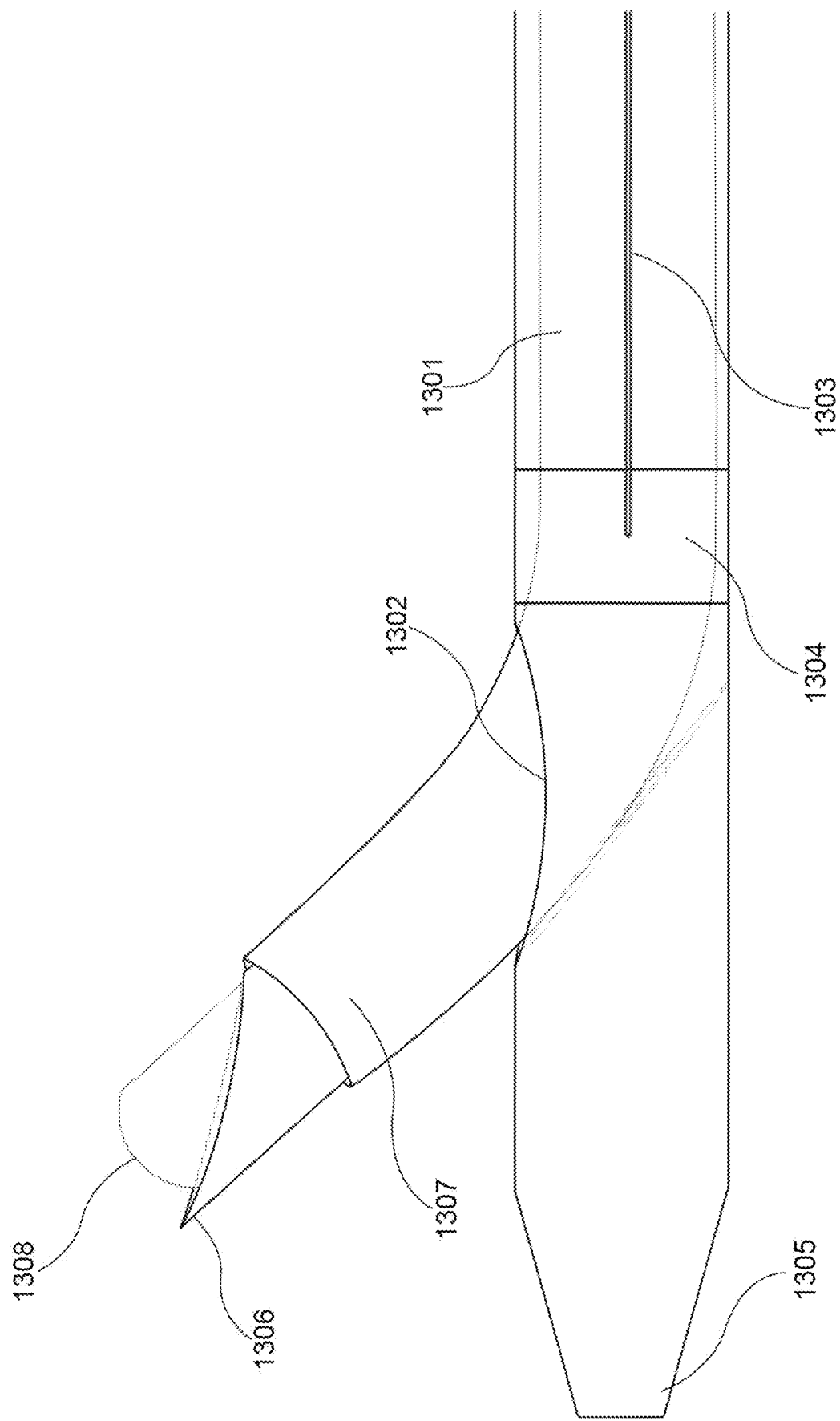
FIG. 13 illustrates an embodiment of the transvascularly-introduced steerable catheter in accordance with some embodiments of the present disclosure.

FIG. 13 illustrates an embodiment of the transvascularly-introduced steerable catheter, a lateral wall working exit lumen port deployed flexible biopsy needle, and a through-the-needle deployed microcatheter housing single and/or multimode optical fibers for in situ imaging, sampling, and/or ablating of tissue/media in accordance with an embodiment of the present disclosure.

Illustrated in FIG. 13 is a steerable catheter shaft 1301 with a lateral wall working exit lumen port 1302, a pullwire 1303, and a steering collar 1304. The steerable catheter includes an atraumatic tip 1305. A flexible needle 1306 with needle sheath 1307 may be introduced via the steerable catheter. Further, fiber optic equipped microcatheter 1308 may be introduced via the steerable catheter. The fiber optic equipped microcatheter 1308 may be configured for locally sensing, stimulating, collecting, and/or ablating tissue and/or media.

Figure 14:
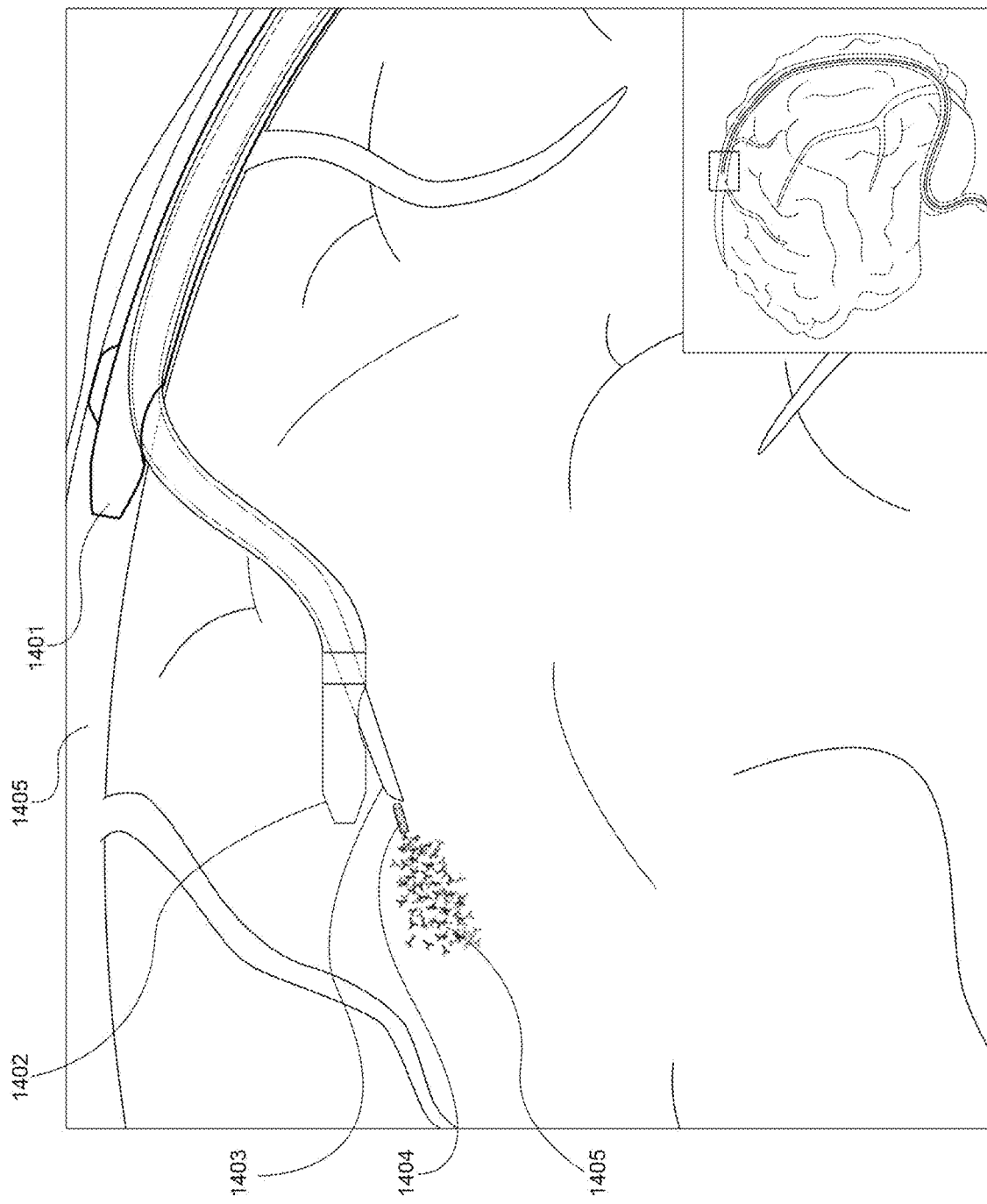
FIG. 14 illustrates a process and an embodiment of the access catheter device mediating extravascular navigation in accordance with some embodiments of the present disclosure.

FIG. 14 illustrates a process and an embodiment of the access catheter device mediating extravascular navigation with a transvascularly-introduced steerable catheter, a lateral wall working exit lumen port deployed flexible biopsy needle, and an injectable nanofluidic device bioresorbable implant for sustained, dose-controlled release of cyto-active agents/compounds within the subarachnoid space in accordance with an embodiment of the present disclosure.

Depicted in FIG. 14 is an embodiment of a transvascular access/guide catheter with offset balloon 1401, and a steerable catheter 1402. The steerable catheter 1402 is deployed into the subdural space from the lateral wall exit lumen port of guide/access catheter. A flexible needle 1403 may then be deployed from the steerable catheter's lateral wall working exit lumen port. The flexible needle 1403 may be used to implant a sustained dose-controlled release bioresorbable nanofluidic capsule 1404. Additionally, local antibody therapy dispersion may be dispensed from nanofluidic device channel 1405. The catheter assembly may be positioned within the cerebral vein or sinus 1406, including, but not limited to, the superior sagittal sinus.

Figure 15:
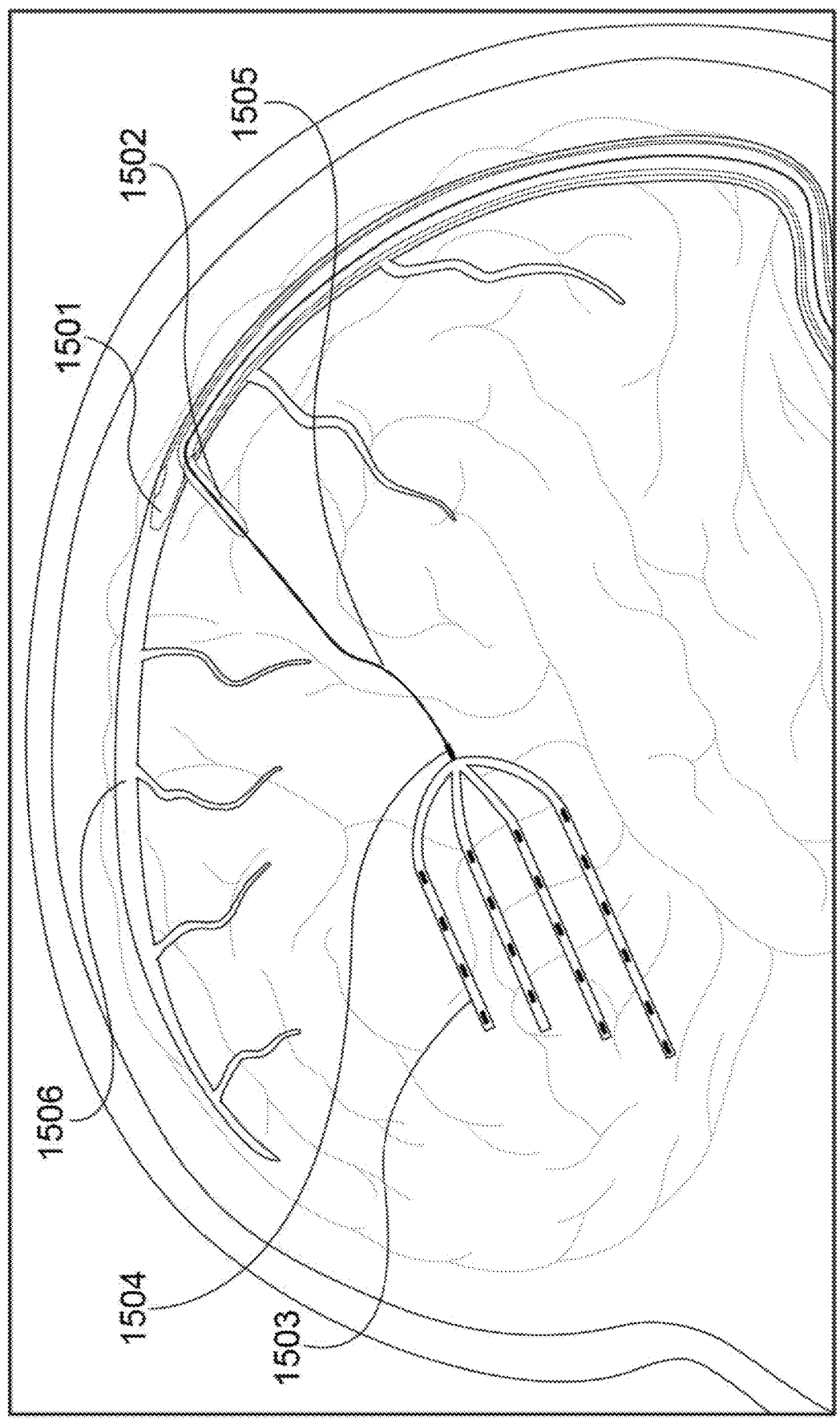
FIG. 15 illustrates a process and embodiment of an access catheter device mediating extravascular navigation with a transvascularly-introduced steerable catheter deploying an embodiment of a highly compressible, shape memory planar electrocorticography implantable array in accordance with some embodiments of the present disclosure.
Figure 16:
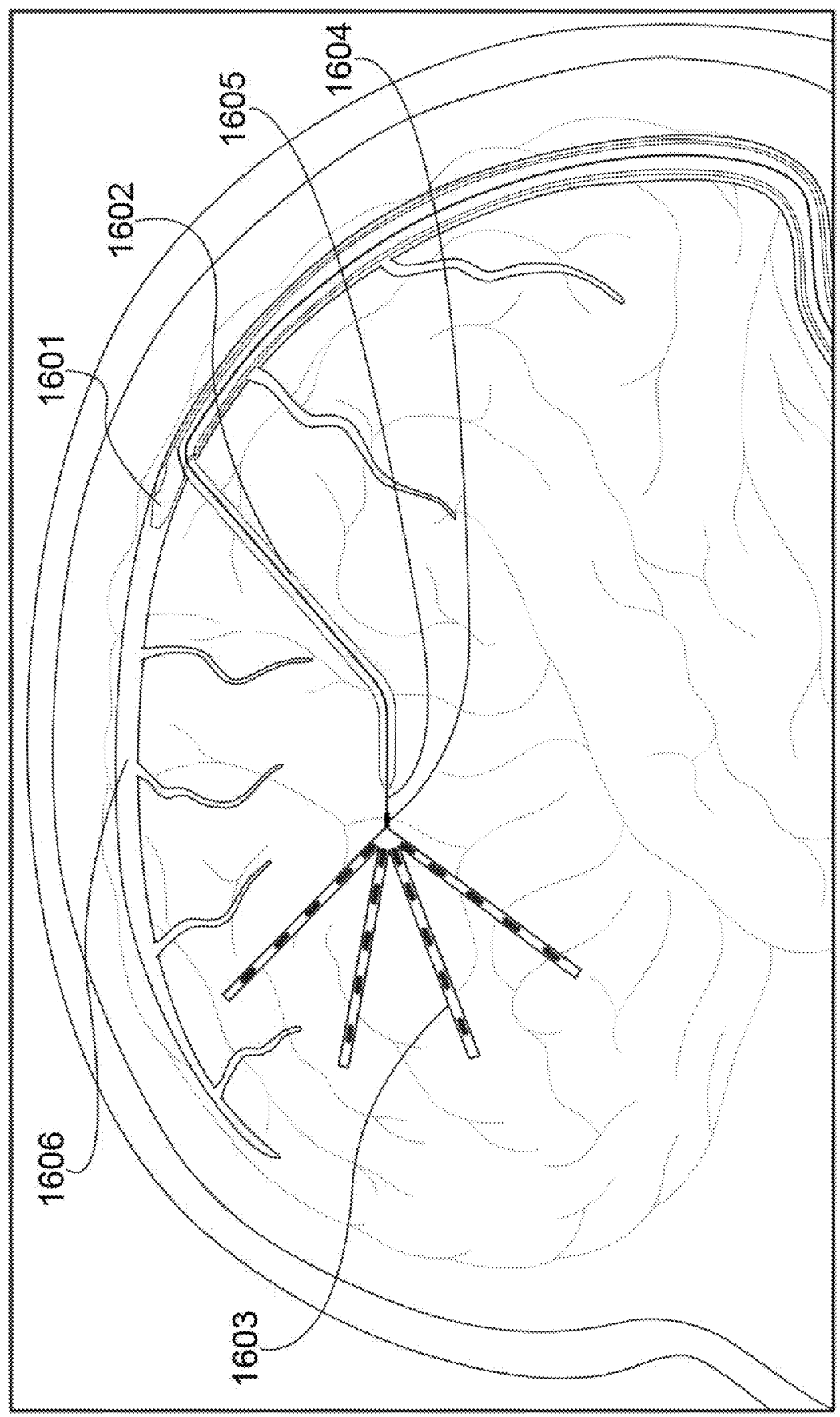
FIG. 16 illustrates a process and embodiment of an access catheter device mediating extravascular navigation with a transvascularly-introduced steerable catheter extravascularly deploying an embodiment of a highly compressible and micro- or self-actuating planar electrocorticography implantable array in accordance with some embodiments of the present disclosure.
Figure 17:
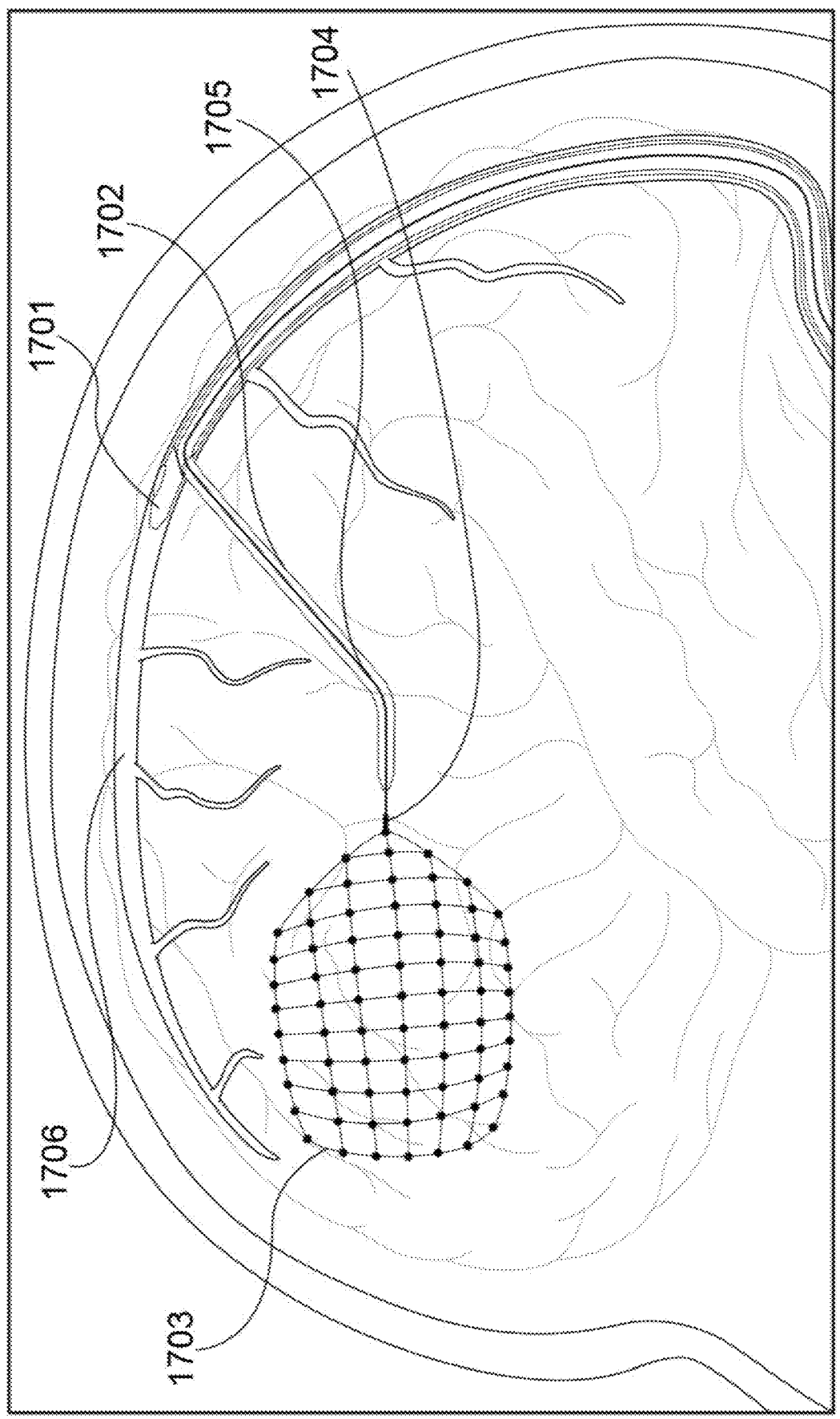
FIG. 17 illustrates a process and embodiment of an access catheter device mediating extravascular navigation with a transvascularly-introduced steerable catheter deploying an embodiment of a highly compressible and self-expanding conformable, planar microelectrocorticography implantable array in accordance with some embodiments of the present disclosure.

FIGS. 15-17 illustrate processes and embodiments of the access catheter device used in connection with catheter-deliverable micro-electrocorticography arrays. In some embodiments, the deployment catheter may be proximally retracted, trailing a multi-conductor lead transvascularly to the percutaneous access site, then outside of the patient, and then the puncture may be closed around the lead.

The lead may have a connector for removable connection to a control system that may be in a housing attached to the patient such as by straps or an adhesive in the case of an ambulatory patient, or a desktop unit as desired.

The ambulatory patient control may include a power supply, processor and a memory for retaining programmed operating parameters and/or storing sensed patient data. In some implementations the control may include sensing circuitry for sensing an electrical parameter in the brain and generating a responsive, therapeutic signal for delivery to the brain via the electrode array. In some embodiments, the array may be anchored within the vein and be powered or transmit wirelessly via microengineered coils or chips.

FIG. 15 illustrates a process and embodiment of an access catheter device mediating extravascular navigation with a transvascularly-introduced steerable catheter deploying an embodiment of a highly compressible, shape memory planar electrocorticography implantable array in the subdural space over the cortical surface of the brain optimally configured for modulating neuronal activity over a functional neuroanatomical zone in accordance with an embodiment of the present disclosure.

As depicted, an embodiment of transvascular access/ guide catheter with offset balloon 1501 may be used for the deployment of a electrocorticography array. The steerable catheter 1502 may be deployed into the subdural space from the lateral wall exit lumen port of guide/access catheter being retracted. The catheter may be configured to deliver a super-elastic shape memory thin film electrocorticography array 1503 connected to a wire bundle connector 1504. The wire bundle 1504 may be encased in a shape memory hypo-tube 1505. The entire assembly may be positioned within the cerebral vein or sinus 1506 such as the superior sagittal sinus. The embodiment illustrated in FIG. 15 may be optimally configured for modulating neural activity over a functional neuroanatomical zone.

FIG. 16 illustrates a process and embodiment of an access catheter device mediating extravascular navigation with a transvascularly-introduced steerable catheter extravascularly deploying an embodiment of a highly compressible and micro- or self-actuating planar electrocorticography implantable array in the subdural space over the cortical surface of the brain optimally configured for mapping activity over a large spatial extent and across distinct functional neuroanatomical boundaries in accordance with an embodiment of the present disclosure.

As illustrated an embodiment of transvascular access/guide catheter with offset balloon 1601 may be used. A steerable catheter 1602 may be deployed into the subdural space from the lateral wall exit lumen port of guide/access catheter being retracted. The catheter may be configured to deliver a super-elastic shape memory thin film electrocorticography array 1603 connected to a wire bundle connector 1604. The wire bundle 1564 may be encased in a shape memory hypo-tube 1505. The entire assembly may be positioned within the cerebral vein or sinus 1606 such as the superior sagittal sinus. The embodiment illustrated in FIG. 16 may be optimally configured for mapping neural activity over a large spatial extent and across distinct functional neuroanatomical boundaries.

FIG. 17 illustrates a process and embodiment of an access catheter device mediating extravascular navigation with a transvascularly-introduced steerable catheter deploying an embodiment of a highly compressible and self-expanding conformable, planar microelectrocorticography implantable array in the subdural space over the cortical surface of the brain optimally configured for direct, high resolution central neural interfacing in accordance with an embodiment of the present disclosure.

As illustrated in FIG. 17, a transvascular access/guide catheter with offset balloon 1701 may be used to deliver a self-expanding mesh electrocorticography array 1703. A steerable catheter 1702 may be deployed into the subdural space from the lateral wall exit lumen port of the guide/access catheter 1701 being retracted. The electrocorticography array 1703 may be connected by a wire bundle connector 1704, where the wire bundles may be encased in a shape memory hypo-tube 1705. The assembly may be positioned within the cerebral vein or sinus 1706, including for example, the superior sagittal sinus.

Figure 18A:
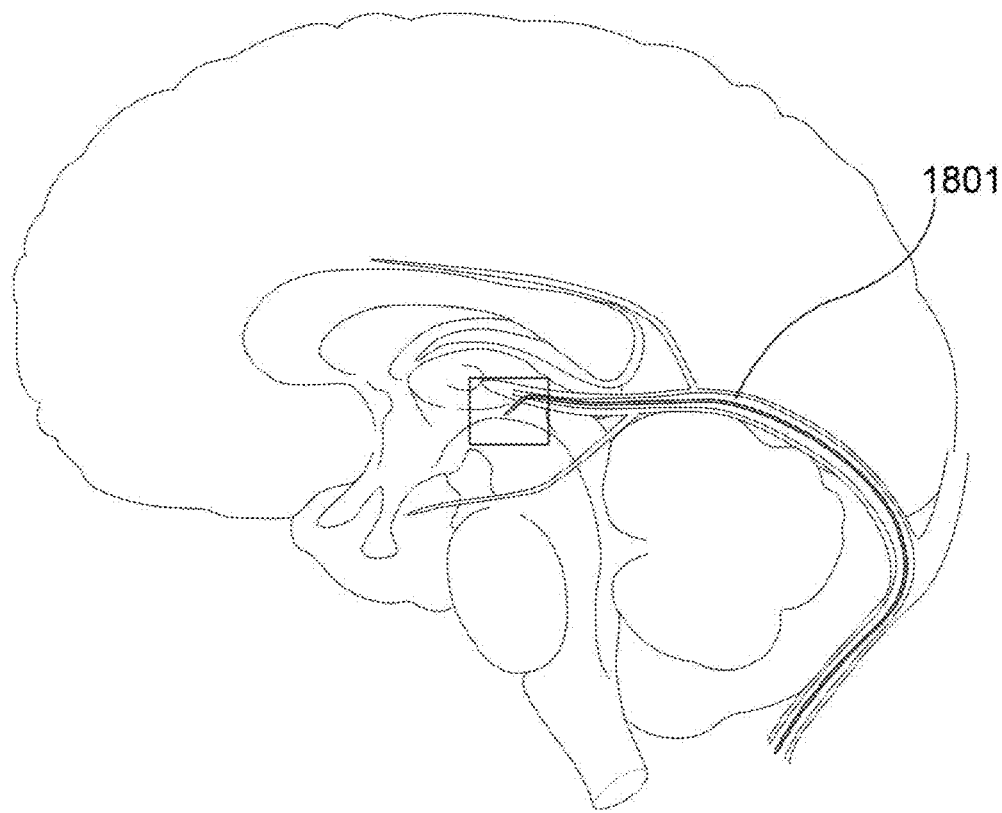
FIG. 18A illustrates first view of an embodiment of the hybrid-sized catheter device residing in a deep cerebral vein transvenously delivering a submillimeter, wireless (i.e., energy harvesting, near field radiofrequency, etc.) deep brain stimulator implant in accordance with some embodiments of the present disclosure.
Figure 18B:
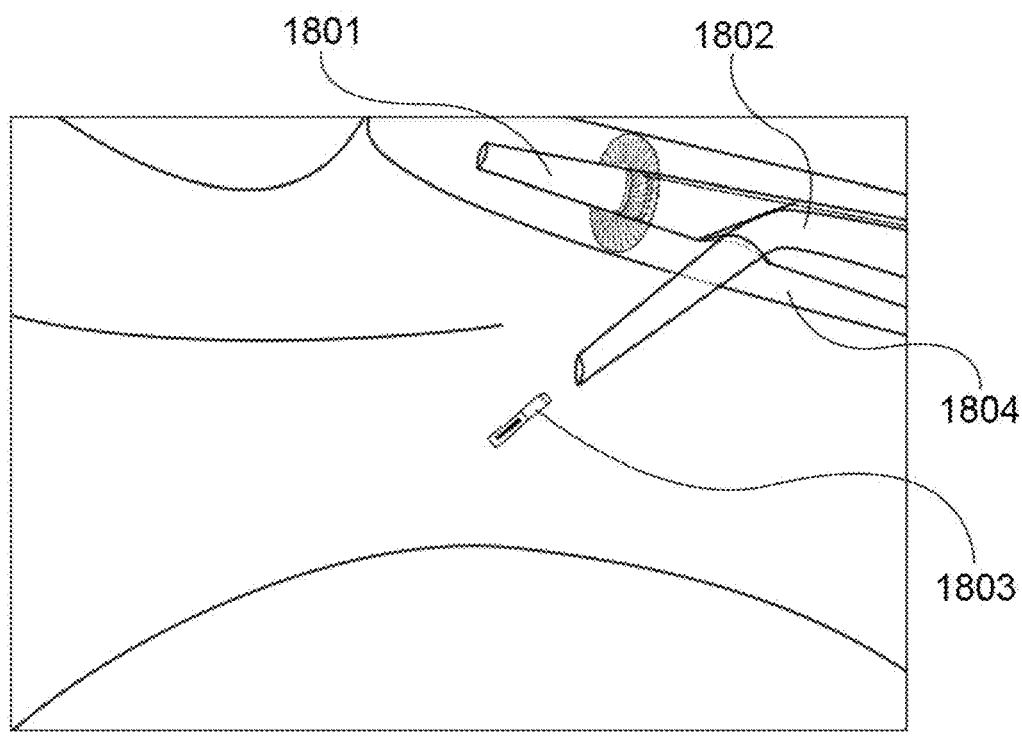
FIG. 18B illustrates second view of an embodiment of the hybrid-sized catheter device residing in a deep cerebral vein transvenously delivering a submillimeter, wireless (i.e., energy harvesting, near field radiofrequency, etc.) deep brain stimulator implant of FIG. 18A in accordance with some embodiments of the present disclosure.

FIGS. 18A and 18B illustrate an embodiment of the hybrid-sized catheter device residing in a deep cerebral vein transvenously delivering a submillimeter, wireless (i.e., energy harvesting, near field radiofrequency, etc.) deep brain stimulator implant through a penetrating member deployed from the lateral wall working exit lumen port directly into subcortical nuclei in accordance with an embodiment of the present disclosure.

Illustrated in FIGS. 18A and 18B is an embodiment of a transvascular hybrid-sized catheter with distal expandable non-occlusive mesh balloon 1801. A steerable catheter 1802 may be deployed into the subdural space from the lateral wall exit lumen port of guide/access catheter 1801 being retracted. The catheter 1802 may be used to deliver a wireless submillimeter deep brain stimulator 1803. The assembly may be positioned within the cerebral vein and sinus 1804, including for example, the internal cerebral vein.

The embodiments, methods and transvascularly introduced catheters described herein may be steered or guided through the subdural space to remote sites located centimeters away from the transvascular puncture site for precise and pre-specified delivery to target intracranial sites, tissues, or media representing a significant advancement over current methods/systems. Increasing the weave density or picks per inch of the transvascularly introduced steerable catheter can improve its trackability and navigability through the subdural/subarachnoid space. Steerable functionality may comprise pullwire(s) laser welded to a steering collar or a ferromagnetic tip deflectable via applied magnetic fields. By increasing the number of pull-wires or the thickness of the pull-wires, enough tensile strength may be conferred to the steerable catheter enabling it to remain in a precise configuration at/near a target site despite the introduction of catheters, instruments, or tools that can impose loading forces within the steerable catheter lumen.

The use of a balloon near the distal end of catheter wall and/or opposite the lateral wall working exit lumen port, or deployed from the distal end working exit lumen port of the catheter, also provides a mechanism for postprocedural hemostasis. In some embodiments, a bioabsorbable hemostatic material includes least one of Poly (L) polymer, and Dextran-Sucrose-Sodium Citrate polymer may be used when balloon inflation insufficiently provides hemostasis. In some embodiments, a catheter with advanced functionality includes at least one of: a steerable catheter; a steerable needle; a flexible needle sheathed in a steerable catheter or a protective tubular member; a catheter housing fiber optic and related elements; a catheter with an imaging or an ablative optical fiber; a catheter housing a complementary metal-oxide semiconductor and related elements; a catheter designed to deliver and/or retrieve a biopotential sensing/stimulating/modulating device; a drug delivery microcatheter for convection enhanced drug delivery; or a catheter configured to deliver a nano/micro-fluidic apparatus.

Embodiments associated with the present disclosure may include approaches, techniques, and methods that reduce the invasiveness, collateral damage, and mistargeting associated with conventional techniques for accessing brain and related intracranial tissue or media for the diagnosis and treatment of seizure disorder, brain cancer, infection, inflammation, degeneration, psychiatric disease, memory or motor impairment, or movement disorder.

Embodiments of the present disclosure may include a method for providing transvenous access to a brain. In some embodiments, a method for providing transvascular access to a brain includes the steps of: 1) positioning a first guide/access catheter within a vessel via a guiding mechanism, such as a microcatheter and microguidewire enabling passive traction or ferromagnetic distal tip structure enabling remote electromagnetic guidance, wherein the first catheter comprises a lumen, an extra-axial expandable structural member, and a lateral wall working exit lumen port; 2) inflating balloon(s) or expanding a compliant mesh structure on the first catheter; 3) deploying a second catheter or advanced function catheter (e.g., penetrating catheter or needle sheathing catheter) through the lateral wall of the working exit lumen port; 4) deploying and/or unsheathing the needle, puncturing across the vein, creating a venous puncture site, and advancing a second steerable or remotely guided catheter into a target area; 5) transcatheter deployment of device(s) to either collect tissue, deliver drugs, implant devices, record from neurons, modulate neuronal activity, or ablate tissue; 6) removing the second catheter, and deflating the balloon(s) or compressing the expandable mesh of the first catheter; 7) repositioning the first catheter such that at least one of the deflated balloons overlays the venous puncture site or inflating a balloon on or at the distal end of a catheter; 8) inflating a balloon positioned over the transvascular puncture site for direct tamponade; 8) evaluating if hemostasis has been achieved by deflating the balloon(s); 9) deploying a biosynthetic, bioresorbable hemostatic material from an exit port over the transvascular access site from a co-axial catheter emanating from an exit lumen port of the endovascular catheter in response to poor hemostastic control.

Optionally, the endovascular guide/access catheter has an outer diameter between about 1.3-2.2 mm (3.9 to 6.6 French). In some embodiments, the working lumen exit port(s) can have a diameter between about 0.4-1.95 mm. Optionally, the catheter may feature reinforced tubing with a variable weave density, picks per inch, or pitch between about 0.005-0.1, 20-250, or 0.015-0.006, respectively, along specific segments of the catheter shaft. Optionally, the internal luminal moldings may have an angle from the horizontal plane between about 15-60 degrees. Optionally, expandable structure member(s) can have an outer diameter between about 0.8-5 mm. Optionally, the balloon(s) includes at least one of polyurethane, chlonoprene, and silicone. Optionally, the expandable mesh structural member(s) can be a shape memory alloy/material (e.g., Nitinol). Optionally, the expandable mesh structural member(s) can be conformally coated with parlyene, polyether-ketone, or polyurethane.

In some embodiments, the second catheter with advanced functionality deployed from the lateral wall lumen exit port includes at least one of a preformed shape memory catheter, a steerable catheter or needle, a flexible needle sheathed in a steerable catheter, a catheter housing a fiber optic imaging, sensing, or stimulating probe, a catheter encasing an ablative thermal therapy fiber optic probe, a transcatheter implant retrieval device, a drug delivery microcatheter, and a drug-eluting nanofluidic implant.

Optionally, the second catheter device with advanced functionality can have an outer diameter between about 0.4-1.95 mm and an inner diameter between about 0.3–1.92 mm. Optionally, the second catheter may be co-axial to the first catheter. Optionally, the bioabsorbable material further includes at least one of Poly (L) polymer, and Dextran-Sucrose-Sodium Citrate polymer.

Embodiments of the present disclosure are directed towards a device, and related systems and methods for transvascular access to the brain and more particularly to catheter-based systems and methods useable for directly accessing tissue/media contents within the intracranial vault, local drug delivery, tissue biopsy, media sampling/collection, device/implant delivery, or energy delivery for imaging, sensing, stimulating, modulating, or ablating abnormal brain tissue and the like without burr holes or craniotomy. Brain tissue may include neurons, glia, or their constituent components, as well as benign or malignant tissue(s) that originate from the brain or spine, or from an exogenous/extracranial organ (metastatic lesion) source. Although embodiments of the present disclosure are discussed in relation to access to brain tissue, it is envisioned that the disclosed areas may be modified for use with other areas.

In some embodiments, the expandable structural elements are configured to have a diameter or radius in the range of approximately 0.5-6 mm. In some embodiments, the working lumen exit port may have a diameter ranging between 0.4-1.95 mm. In some embodiments, the catheter lumen 105 may have a diameter of approximately 0.4-2.0 mm. In some embodiments, a first, proximal expandable structure 101 and a second, distal expandable structure 103 may be of the same diameter. In alternative embodiments, the first proximal expandable structure and the second, distal expandable structure may have different sizes.

In some embodiments, the expandable structural elements may be composed of compliant or ultra-compliant material exerting less than 400 mm Hg of pressure, which is below the radial force threshold associated with vein rupture or laceration of the vein (>600 mg Hg).

In some embodiments, the expandable element(s)/structure(s) may be spherical, toroidal, rectangular, cylindrical, or variable in shape. Further, expandable structures may be composed of silicone, polyurethane, chlonoprene, or cross-linked nitinol and the like. Spherical expandable element(s)/structure(s) are illustrated in some embodiments because this shape may have more predictable inflation parameters and may be more widely available or engineered. The catheter may or may not feature spherical balloons.

In some embodiments, the expandable elements/structures (e.g., elastomeric balloons or expandable nitinol 3D structure) in the described system are configured to prevent vascular blood flow from entering into the perivascular and subdural/subarachnoid space(s) once transvascular access is obtained.

Advantageously, positioning the lateral wall working lumen exit port between the two balloons may also temporarily occlude physiological vascular blood flow, as well as prevent retrograde negative-pressure gradient vascular blood flow from downstream nearby branching tributaries or caudal channels from entering into the perivascular/subdural/subarachnoid space(s).

In some embodiments, the access/guide catheter discussed herein may feature only single expandable structural element/member distal to the lateral wall working exit lumen port, which may temporarily minimize blood flow or occlude a draining vein upstream and distal to the lateral wall working exit lumen port.

In comparison to conventional systems mediating neuroendovascular access and transcatheter instrumentation, the disclosed systems include a lateral wall working lumen exit port configured proximal to, between, or opposite to compressible-expandable structural element(s)/member(s). Further, in comparison to conventional systems mediating transvascular access, the disclosed systems allow for neuroendovascular use and more particularly, distal venous access within the intracranial vault, as well as allows for the co-axial introduction of penetrating instruments and/or additional catheters from the lateral wall working exit lumen port for transmural/transvascular, subdural/subarachnoid, brain parenchymal entry/access/navigation.

In some embodiments, the disclosed catheter device may act as a conduit for co-axially-introduced catheters with or without advanced functionality, such as a flexible needle or needle sheathed in a protective tubular housing unit or catheter, a fiber optic ablation mini-endoscope or catheter, an imaging probe or catheter, a pre-shaped or a steerable catheter for targeted deployment of an implantable electrode array (such as a self-expanding, shape memory, or flexible electronic) or a catheter-deliverable micro/nano-fabricated device (such as sustained release drug-eluting nanofluidic seed implant or wireless submillimeter deep brain stimulator).

Advantageously, positioning the lateral wall working lumen exit port opposite to the complaint expandable balloon or mesh structures may juxtapose penetrating instruments or members deployed from the lateral wall working exit lumen port against the endoluminal surface of the intended venous puncture site to prevent the infiltration of vascular blood flow into the perivascular/subdural/subarachnoid space(s).

Advantageously, positioning the lateral wall working lumen exit port between the two balloons may also temporarily occlude physiological vascular blood flow, as well as prevent retrograde negative-pressure gradient vascular blood flow from downstream nearby branching tributaries or caudal channels from entering into the perivascular/subdural/subarachnoid space(s).

In some embodiments, the access/guide catheter disclosed herein may feature only single expandable element/structure distal to the lateral wall working exit lumen port, which may temporarily minimize blood flow or occlude a draining vein upstream and distal to the lateral wall working exit lumen port and allowing for a second catheter to be introduced co-axially to mediate the transvascular puncture procedure and transvascular catheter or transcatheter device introduction.

In some embodiments, the guidewire may include a hydrophilic-coated metal guidewire having a 0.014 inch, 0.018 inch, or similar diameter and a variable length. For example, the variable length may be between 80 to 300 cm. A guidewire introduced through a microcatheter configured to extend along the central lumen through to the distal exit port to position the embodied transvascular guide/access catheter device(s). Alternatively or in conjunction, the catheter or microcatheter may feature steerable properties and external control actuators (e.g., wire pulley system or magnetically-guided catheter tips).

In some embodiments, including, but not limited to those illustrated in FIGS. 8, 10, 12, 14-18), the access/guide catheter accommodates a second catheter equipped or adapted with advanced-functionality (e.g., a steerable needle, a flexible needle sheathed in a steerable catheter, flexible needle or catheter with optical imaging, ablative, and/or a transcatheter deliverable detachable flexible electroceutical, drug delivery microcatheter or fluidic chamber, etc.) to be deployed from its lateral wall working exit lumen port. The lateral wall working exit lumen port allows for the passage and deployment of catheters with advanced-functionality or other related instrumentation across the vessel wall into an extravascular target tissue/space trajectory. The wire deployed from the penetrating member can guide/specify the transvascular target entry site aided by the anchoring placement of the guide/access catheter by expansion of compliant structural element(s)/member(s).

Further endothelial repair material may be deployed from a working exit lumen port to patch and/or repair the transvascular access site for hemostasis. In some embodiments, expandable structural member(s)/element(s) may be compliant or super-compliant (e.g., polyurethane, chloroprene, silicone, or nitinol mesh) so as to prevent vessel rupture, laceration, or dissection on inflation. Inflatable balloons may be configured to prevent venous blood flow from entering the space occupied by the lateral wall working exit lumen port or the venous puncture site.

In some embodiments compliant balloon catheter element(s)/member(s) may be facilitate the transvenous access procedure by concealing or isolating the lateral wall working exit lumen port from venous blood flow without occluding the vein entirely to allow needle or transvenous catheter insertion. In some embodiments, in order to perform its intended function the disclosed catheter would feature a smaller outer diameter (e.g., less than 2.5 mm) for use in the cerebral veins. Balloon shape may vary, but it principally functions to minimize blood infiltration into the brain parenchyma, subdural or subarachnoid spaces from the transvascular puncture site. Any variety of shapes may accomplish this.

In some embodiments, the catheter may be configured to be straight without angulation or curvature. Such a catheter may be configured to taper over a variable length (e.g., 1-5 cm) and provide access in draining veins that would not accommodate a wider lumen catheter. The tapered end would may feature a wire lumen to non-traumatically guide the catheter to a deep cerebral or small diameter cortical draining veins. Alternative steering mechanisms may be employed (e.g., steerability via pull-wires or magnetic guidance). It provides the advantage of a balloon occluding the cerebral vein distally without having to access the entire vein with the large lumen end of the catheter. It would in essence enable transvenous access with a larger lumen co-axial catheter to veins with a rapidly tapering diameter.

In some embodiments a catheter may include a distal compliant expandable wire mesh operably connected to pullwire housed in a segregated lumen for transvenous access that is configured to anchor the site of the lateral wall working exit lumen port without occluding the vein entirely so as to allow penetrating member and/or catheter deployment. In order to perform its intended function the distal end of the proposed catheter would feature a smaller outer diameter (e.g., less than 1.1 mm) for use in the deep cerebral veins.

In some embodiments, the torqueable catheter may include a tip that is torqueable via two wires flanking diametrically opposed ends of the catheter lumen. The two wires may operate via a pulley system enabling proximal torque application for distal steerability.

In some embodiments the working lumen exit port supports the introduction of a steerable catheter or sheathed flexible needle that is configured to reduce the required insertion force. Further the catheter may be capable of dilating the transvenous access site and allowing for close approximation of the distal end of the adapted-catheter with advanced-functionality exiting the working lumen exit port, which in turn allows for transvenous cannulation beyond the perivenular space and into the target tissue site or subdural/subarachnoid space. The unsheathed flexible needle and housing catheter can then be completely retracted from the perivascular space while affixing/approximating the distal end of a co-axial catheter at the transluminal cannulation site. A catheter will protrude from the working lumen exit port to enable transvenous access from an endovascular site whilst its distal end is positioned near/into the perivascular/subdural/subarachnoid space.

In some embodiments, the transvenously affixed/abutted catheter may allow for the introduction of a flexible biopsy needle, ablation catheter with in situ imaging capabilities, chemotherapeutic/immunomodulatory drug delivery via catheter or implant, or insertion of a catheter deliverable recording/stimulating electrode lead or expandable cortical microelectrode array to be directly introduced to/over brain tissue and, in those instances where it is clinically indicated, later withdrawn.

Upon completion of the transvenous procedure the balloon may be deflated, repositioned, and re-inflated, or in some cases a biodegradable material will be deployed to overlay the puncture site and prevent intraparenchymal hematoma formation by sealing the endoluminal venous puncture site.

In some embodiments, the biodegradable biopolymer material may include one or more of Poly (L) polymer, Dextran-Sucrose-Sodium Citrate polymer, and the like. The mesh may be square, oval, or cylindrically shaped. In some embodiments the surface area of the nanofiber mesh may be large enough to patch the venous entry site (e.g., 0.5 mm to 2 mm squared).

In some embodiments, the disclosed catheters and related components may be sized appropriately to provide transvenous cannulation and/or access. In particular, in some embodiments the endovascular balloon catheter may be scaled to between 2.4 French to 6 French (0.8-2.0 mm) size, depending on the vein that is to be accessed. Additionally, coaxially introduced catheters may feature a length at least 10 cm beyond the length of the endovascular balloon catheter and an outer diameter at least 0.003 inch smaller than the endovascular balloon catheter working exit lumen port inner diameter.

In some embodiments, the disclosed flexible needle may be fabricated and interspersed with flexible elements. A wire pulley system will enable its sheathing catheter to maneuver the needle in its intended incident angle trajectory.

In some embodiments, the apparatus, methods, and systems associated with the present disclosure may be used in connection with dynamic imaging techniques and reliable fiducial markers located in proximity to the tissue of interest so as to better target the brain tissue of interest (e.g., the lesion or anatomical substrate of interest).

Additionally, specific anatomical locations, such as the posterior fossa and the presence of coagulopathic risk factors may discourage the use of conventional methods such as open surgical and current stereotactic methods for accessing brain tissue. A method for overcoming these barriers provides advantages to the healthcare system, such as improvement in tissue diagnosis to tailor treatment and potentially cure disease, decreased length of hospital stay and complication rate, and increased patient satisfaction.

In some embodiments, the catheter may be deployed by first using standard percutaneous central venous access via either the subclavian vein, femoral vein, or internal jugular vein. Then the 6 French access balloon catheter may be advanced over microguidewire-microcatheter system in telescoping coaxial configuration to a cerebral vein, such as the Superior Sagittal Sinus. Further, the working lumen exit port site may be positioned over intended venous puncture site from within the endolumen of the vein. Then an imaging optical fiber, ultrasound, or microcamera probe equipped flexible needle may be advanced through the working exit lumen port of the access catheter to the intended venous puncture site from the endolumen of the vein over a microguidewire to enable in situ imaging. Then the extra-axial support structures may be expanded to minimize venous physiologic drainage and backflow across the venous puncture site. Then a flexible/steerable needle and/or catheter may be equipped with an imaging fiber optic, ultrasound, or microcamera probe may be advanced through the working lumen exit port. Next, a flexible/steerable needle may perform a transvenous puncture from an endoluminal site to the extravascular space. Next, a flexible needle and its corresponding sheathing catheter or guard may be removed while retaining a guide wire in place to re-locate the puncture site. Next, a steerable catheter, which may feature an imaging fiber optic probe, ultrasound transducing, or video microcamera may be introduced over the guidewire into an extravascular space, after which the guidewire may be removed.

If deployed within the subarachnoid space, the arachnoid trabeculae may be mechanically sheared or ablated and/or the microvasculature in subarachnoid space where a medical device is to be deployed may be cauterized. The catheter may be removed, such that a distinct device delivery catheter may be introduced. In next steps, a device may be introduced through a steerable device delivery catheter. After the device is introduced it may be deployed and the steerable device delivery catheter may be removed.

In a next step, a hemostatic biodegradable mesh or stent may be delivered over the venous puncture site if the balloon tamponade does not create hemostasis. The balloon catheter can then be deflated and removed. In a last step a wire bundle configured to power, transmit to and/or receive signals from the electrode array may be subcutaneously attached to an implantable battery and/or transponder pack in the thorax.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A system for providing transvascular access to an extravascular site, comprising:
   an access catheter for supporting transvascular access, the access catheter comprising:
      an elongate tubular body having a proximal end, a distal end, and a lumen extending between the proximal end and the distal end, the distal end comprising an atraumatic tip;
      an inclined barrier within the lumen at a distal portion of the elongate tubular body;
      an aperture passing through the inclined barrier, the aperture having an aperture diameter; and
      a side exit port in the elongate tubular body, in communication with the lumen and located proximally adjacent to the inclined barrier, the side exit port having a transverse dimension at a longitudinally central portion of the side exit port, wherein the aperture diameter is less than the transverse dimension, wherein the access catheter further comprises a laterally expandable support carried on the elongate tubular body on an opposite side of the elongate tubular body from the side exit port and diametrically opposite to the side exit port, and wherein the laterally expandable support has an unexpanded state and an expanded state, and wherein the laterally expandable support is configured to expand from the unexpanded state toward the expanded state in a first radial direction against a first side of a vessel wall of a blood vessel, thus causing the side exit port and a portion of the elongate tubular body surrounding the side exit port to be forced in a second radial direction, opposite the first radial direction, such that the side exit port and the portion of the elongate tubular body are positioned against a second side of the vessel wall, opposite the first side.

2. The system of claim 1, wherein the laterally expandable support comprises an inflatable balloon.

3. The system of claim 2, wherein the inflatable balloon comprises an elastomeric balloon.

4. The system of claim 1, wherein the laterally expandable support comprises at least one laterally deflectable strut.

5. The system of claim 1, wherein the lumen has a lumen diameter, and wherein the lumen and the side exit port are configured to cooperatively allow the passage through the side exit port of a flexible elongate device having a device diameter less than the lumen diameter and less than the transverse dimension, but greater than the aperture diameter.

6. The system of claim 5, wherein the lumen and the side exit port are configured to allow the passage though the side exit port of at least some elongate devices having diameters of greater than 0.90 mm.

7. The system of claim 1, wherein the elongate tubular body has a horizontal plane, and wherein the inclined barrier has an angle of inclination from the horizontal plane of between 15° and 60°.

8. The system of claim 1, further comprising:
an elongate device comprising a penetrating member, configured for placement into the lumen, wherein the access catheter is configured to direct the elongate device out the side exit port.

9. The system of claim 1, further comprising:
an elongate device comprising an ablation device, configured for placement into the lumen, wherein the access catheter is configured to direct the elongate device out the side exit port.

10. The system of claim 1, further comprising:
an elongate device comprising an imaging device, configured for placement into the lumen, wherein the access catheter is configured to direct the elongate device out the side exit port.

11. The system of claim 1, further comprising:
an elongate device having a distal end comprising an electrocorticography array, the distal end of the elongate device configured for placement into the lumen.

12. The system of claim 11, wherein the access catheter is configured to direct delivery of the electrocorticography array out the side exit port.

13. The system of claim 11, wherein the electrocorticography array is a planar array.

14. The system of claim 11, wherein the electrocorticography array is compressible.

15. The system of claim 11, wherein the electrocorticography array comprises a shape memory alloy.

16. The system of claim 11, wherein the electrocorticography array is configured for extravascular placement into or onto the brain of a patient.

17. The system of claim 11, further comprising:
a delivery catheter having a distal end configured for placement into the lumen, wherein the access catheter is configured to direct the distal end of the delivery catheter out the side exit port.

18. The system of claim 17, wherein the distal end of the elongate device is configured for placement through the delivery catheter.

19. The system of claim 1, wherein the access catheter has an outer diameter of between 1.3 mm and 2.2 mm.

20. The system of claim 1, wherein the access catheter further comprises:
a lubricious inner liner.

21. The system of claim 1, wherein the access catheter has an outer diameter of less than 2.5 mm.

22. The system of claim 1, further comprising:
an elongate device having a tapered distal tip and configured for placement into the lumen, wherein the access catheter is configured to direct the elongate device out the side exit port.

23. The system of claim 1, further comprising:
a delivery catheter having a distal end configured for placement into a lumen, wherein the access catheter is configured to direct the distal end of the delivery catheter out the side exit port, and wherein the delivery catheter is configured to allow the introduction of an elongate device therethrough.

24. The system of claim 10, wherein the imaging device comprises a piezoelectric ultrasound transducer.

25. The system of claim 1, wherein the aperture diameter is sized to permit a catheter having a diameter less than the aperture diameter to pass distally beyond the inclined barrier and out the distal end of the access catheter.

26. The system of claim 1, wherein the laterally expandable support in its expanded state is configured to not occlude the blood vessel.

27. The system of claim 1, wherein the side exit port has a side exit port diameter of between 0.4 mm and 1.95 mm.

28. The system of claim 1, wherein the side exit port is configured to allow a catheter having a diameter of between about 0.4 mm and 1.95 mm to be passed therethrough.

29. The system of claim 1, wherein the lateral expandable support is between about 1 to 20 mm from the distal end of the elongate tubular body.

* * * * *